(12) United States Patent
Csuzdi et al.

(10) Patent No.: US 6,600,036 B2
(45) Date of Patent: Jul. 29, 2003

(54) CONDENSED 2,3-BENZODIAZEPINE DERIVATIVES AND THEIR USE AS AMPA-RECEPTOR INHIBITORS

(75) Inventors: Ernese Csuzdi, Budapest (HU); Tamas Hamori, Budapest (HU); Gizella Abraham, Budapest (HU); Sandor Solyom, Budapest (HU); Istvan Tarnawa, Budapest (HU); Pal Berzsenyi, Budapest (HU); Ferenc Andrasi, Budapest (HU); Istvan Ling, Budapest (HU); Antal Simay, Budapest (HU); Melinda Gal, Budapest (HU); Katalin Horvath, Budapest (HU); Eszter Szentkuti, Budapest (HU); Marta Szollosy, Budapest (HU); Istvan Pallagi, Budapest (HU)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/993,646

(22) Filed: Nov. 27, 2001

(65) Prior Publication Data

US 2002/0052364 A1 May 2, 2002

Related U.S. Application Data

(62) Division of application No. 09/117,508, filed on Nov. 5, 1998, now Pat. No. 6,323,197.

(30) Foreign Application Priority Data

Feb. 1, 1996 (DE) .......................................... 196 04 919
Jan. 29, 1997 (WO) .............................. PCT/DE97/00234

(51) Int. Cl.⁷ .................... C07D 243/10; C07D 487/00; C07D 491/00

(52) U.S. Cl. ......................... 540/495; 540/500; 540/503
(58) Field of Search ................................. 540/495, 500, 540/553

(56) References Cited

U.S. PATENT DOCUMENTS 5,807,851 A   9/1998   Ling et al. .................... 514/221
5,891,871 A   4/1999   Xia et al. ..................... 514/219

FOREIGN PATENT DOCUMENTS

WO   WO 97/34878   9/1997

OTHER PUBLICATIONS

Gatta et al., *Il Farmaco–Ed.Sc.*, vol. 40 (fasc. 12 ) (1983) pp. 942–955.
DeSarro et al., *European Journal of Pharmacology*, 294 (1995), pp. 411–422.

*Primary Examiner*—Bruck Kifle
(74) *Attorney, Agent, or Firm*—Millen, White, Zelano & Branigan, P.C.

(57) ABSTRACT

Compounds of formula I are described, their production and use in pharmaceutical agents.

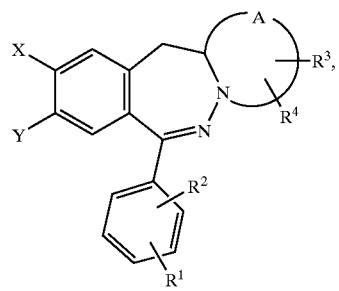

(I)

10 Claims, No Drawings

CONDENSED 2,3-BENZODIAZEPINE DERIVATIVES AND THEIR USE AS AMPA-RECEPTOR INHIBITORS

The invention relates to new 2,3-benzodiazepine derivatives, their production and use as pharmaceutical agents.

It is already known that selected 2,3-benzodiazepine derivatives have modulatory activity at quisqualate receptors and owing to this property are suitable as pharmaceutical agents for treating diseases of the central nervous system.

It has now been found that the 2,3-benzodiazepine derivatives according to the invention are also suitable for treating diseases of the central nervous system, whereby the compounds are distinguished by better properties compared to the above-mentioned prior art.

The invention relates to the compounds of formula I

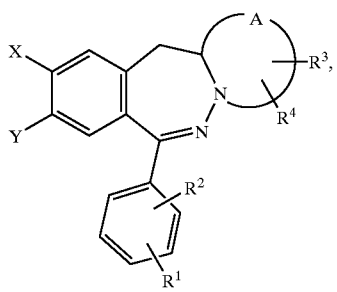

(I)

in which
- $R^1$ and $R^2$ are the same or different and mean hydrogen, $C_1$–$C_6$ alkyl, nitro, halogen, cyano, the group —$NR^8R^9$, —O—$C_{1-4}$ alkyl, —$CF_3$, OH or $C_{1-6}$ alkanoyloxy,
- $R^3$ and $R^4$ are the same or different and mean hydrogen, halogen, $C_1$–$C_6$ alkoxy, hydroxy, thiocyanato, $C_1$–$C_6$ alkylthio, cyano, $COOR^{12}$, $PO_3R^{13}R^{14}$, $C_{1-6}$ alkanoyl, $C_{1-6}$ alkanoyloxy, $C_{2-6}$ alkynyl optionally substituted with $C_{1-4}$ alkoxy or phenyl, $C_{2-6}$ alkenyl optionally substituted with $C_{1-4}$ alkoxy or phenyl; $C_1$–$C_6$ alkyl optionally substituted by halogen, hydroxy, $C_1$–$C_6$ alkoxy, $C_1$–$C_6$ thioalkyl, $NR^{10}$—$R^{11}$; $C_{3-7}$ cycloalkyl, or an optionally substituted aryl or hetaryl radical,
- $R^8$ and $R^9$ are the same or different and mean hydrogen, $C_1$–$C_6$ alkyl or the group —CO—$C_{1-6}$ alkyl,
- $R^{10}$ and $R^{11}$ are the same or different and mean hydrogen, $C_1$–$C_6$ alkyl or $C_{1-6}$ alkanoyl or together with the nitrogen atom form a 5- to 7-membered saturated heterocyle, which can contain another oxygen, sulfur or nitrogen atom and can be substituted,
- $R^{12}$, $R^{13}$, $R^{14}$ are the same or different and mean H or $C_1$–$C_6$ alkyl,
- X means hydrogen or halogen,
- Y means $C_{1-6}$ alkoxy or X and Y together mean —O—$(CH_2)_n$—O—,
- n means 1, 2 or 3, and
- A together with the nitrogen forms a saturated or unsaturated five-membered heterocycle, which can contain 1–3 nitrogen atoms and/or an oxgyen atom and/or one or two carbonyl groups or their isomers or physiologically compatible salts.

Alkyl is defined in each case as a straight-chain or branched alkyl radical, such as, for example, methyl, ethyl, propyl, isopropyl, butyl, isobutyl, sec-butyl, pentyl, isopentyl or hexyl.

$R^3$ and $R^4$ in the meaning of $C_{2-6}$ alkenyl contain at least one double bond such as, for example, vinyl, propenyl, buten-1-yl, isobutenyl, penten-1-yl, 2,2-dimethyl-buten-1-yl, 3-methylbuten-1-yl, hexen-1-yl. If $R^3$ or $R^4$ means $C_{2-6}$ alkynyl, at least 1 triple bond is present, such as, for example, ethynyl, propynyl, butyn-1-yl, butyn-2-yl, pentyn-1-yl, pentyn-2-yl, 3-methylbutyn-1-yl, hexyn-1-yl. The alkenyl and alkinyl radicals can be substituted, e.g., with $C_{1-4}$ alkoxy or phenyl, which can be substituted with halogen. If a halogenated alkyl radical is present, the latter can be halogenated or perhalogenated in one or more places like $CF_3$.

Halogen is defined in each case as fluorine, chlorine, bromine and iodine.

The aryl and hetaryl radicals $R^3$ and $R^4$ can be substituted in one to three places in the same way or differently with halogen, $C_{1-4}$ alkoxy or $C_{1-4}$ alkyl.

The aryl and hetaryl radicals can be present as monocyclic or bicyclic compounds and can contain 5–12 ring atoms, preferably 5–9 ring atoms, such as, for example, phenyl, biphenyl, naphthyl, indenyl as an aryl radical, and thienyl, furyl, pyranyl, pyrrolyl, pyrazolyl, pyridyl, pyrimidinyl, pyridazinyl, oxazolyl, iso-oxazolyl, thiazolyl, isothiazolyl, 1,3,4-oxadiazol-2-yl, 1,2,4-oxadiazolyl-5-yl, 1,2,4-oxadiazol-3-yl, quinolyl, isoquinolyl, benzo[1]thienyl, benzofuranyl as a hetaryl radical with 1–3 heteroatoms such as sulfur, oxygen and/or nitrogen. 2-Thienyl, 3-thienyl, pyridin-2-yl, pyridin-3-yl, pyridin-4-yl and phenyl can be mentioned as preferred.

Cycloalkyl is defined in each case as cyclopropyl, cyclobutyl, cyclopentyl, cyclohexyl and cycloheptyl, especially $C_{3-5}$ cycloalkyl.

As alkanoyl radicals, straight-chain or branched aliphatic carboxylic acid radicals, such as formyl, acetyl, propionyl, butanoyl, isopropylcarbonyl, caproyl, valeroyl, trimethylacetyl, i.a., are suitable.

If $R^{10}$ and $R^{11}$ together with the nitrogen atom form a heterocycle, for example, piperidine, pyrrolidine, thiomorpholine, hexahydroazepine, morpholine, piperazine, imidazolidine, hexahydrodiazepine is mentioned. If the heterocycle is substituted, the substituent $C_{1-4}$ alkyl or phenyl can be in one to two places, such as, for example, N-methyl-piperazine, N-phenyl-piperazine, 2,6-dimethylmorpholine.

If A together with the nitrogen atom forms a saturated heterocycle, the latter can be substituted at the carbon atom or at another nitrogen atom. In this case, A means, for example, $C_3$ alkylene, which can be substituted with $R^3$ and $R^4$, and in which 1, 2 or 3 alkylene groups can be replaced by oxygen, carbonyl or —$NR^3$—, such as, for example, —$(CH_2)_3$—, —$CH_2$—$NR^3$—$CH_2$—, —$CH_2$—O—$CH_2$—, —$CH_2$—O—CO—, —$CH_2$—$NR^3$—CO—, —CO—$NR^3$—CO— or $CH_2$—O—$CR^3R^4$, whereby the carbonyl group is bonded to the nitrogen atom of the benzodiazepine, and $R^3$ and $R^4$ preferably mean $C_{1-4}$ alkyl. These compounds of formula I contain a chiral center in the 4-position of the 2,3-benzodiazepine skeleton and can be present as a racemate or optical isomers.

If A together with the nitrogen atom forms an unsaturated 5-membered heterocycle, it thus is not a chiral carbon atom, but rather an exocyclic double bond that is present in the 4-position of the 2,3-benzodiazepine skeleton. The unsaturated 5-membered heterocycle can be present partially unsaturated or aromatic. Preferred are heteroaromatic compounds with 1–3 nitrogen atoms, in which A has, for example, the following meaning:

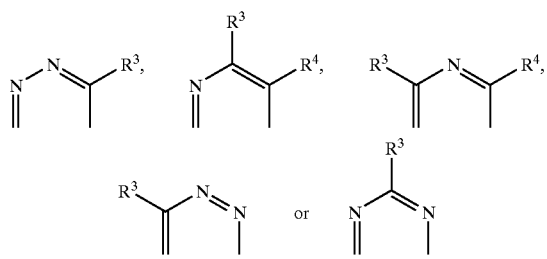

The physiologically compatible salts are derived from inorganic and organic acids. Suitable are inorganic acids, such as, for example, hydrohalic acids such as hydrochloric acid, hydrobromic acid, phosphoric acid, sulfuric acid, or organic acids such as, for example, aliphatic or aromatic mono- or dicarboxylic acids such as formic acid, acetic acid, maleic acid, fumaric acid, succinic acid, lactic acid, tartaric acid, citric acid, oxalic acid, glyoxylic acid or sulfonic acids, for example, $C_{1-4}$ alkanesulfonic acids such as methanesulfonic acid or benzenesulfonic acids that are optionally substituted by halogen or $C_{1-4}$ alkyl, such as p-toluenesulfonic acid.

The compounds of formula I also comprise all possible stereoisomers and their mixtures, such as diastereomers, racemates and enantiomers.

Preferred are compounds of general formula I in which $R^2$ means hydrogen.

The compounds of general formula I as well as their physiologically compatible salts can be used as pharmaceutical agents owing to their non-competitive inhibition of the AMPA receptors. Owing to their profile of action, the compounds according to the invention are suitable for treating diseases that are caused by hyperactivity of excitatory amino acids, such as, for example, glutamate or aspartate. Since the new compounds act as non-competitive antagonists of excitatory amino acids, they are suitable especially for treating those diseases that are influenced by the receptors of excitatory amino acids, especially the AMPA receptor.

The pharmacological action of the compounds of formula I was determined by means of the tests described below:

Male NMRI mice weighing 18–22 g were kept under controlled conditions (0600–1800 hours light/dark cycle, with free access to food and water) and their assignment to groups was randomized. The groups consisted of 5–16 animals. The observation of the animals was performed between 0800 and 1300 hours.

AMPA was sprayed into the left ventricles of mice that were allowed to move freely. The applicator consisted of a cannula with a device made of stainless steel, which limits the depth of injection to 3.2 mm. The applicator was connected to an injection pump. The injection needle was inserted perpendicular to the surface of the skull according to the coordinates of Montemurro and Dukelow. The animals were observed up to 180 sec. until clonic or tonic seizures set in. The clonic movements, which last longer than 5 sec., were counted as seizures. The beginning of the clonic seizures was used as an endpoint for determining the seizure threshold. The dose that was necessary to raise or reduce the seizure threshold by 50% ($THRD_{50}$) was determined in 4–5 experiments. The $THRD_{50}$ and the confidence limit were determined in a regression analysis.

The results of these tests show that the compound of formula I and its acid addition salts influence functional disorders of the AMPA receptor. They are therefore suitable for the production of pharmaceutical agents for symptomatic and preventive treatment of diseases that are triggered by changing the function of the AMPA receptor complex.

The treatment with the compounds according to the invention prevents or delays the cell damage that occurs as a result of disease and functional disorders and reduces the concomitant symptoms.

According to the invention, the compounds can be used for treating neurological and psychiatric disorders that are triggered by overstimulation of the AMPA receptor. The neurological diseases, which can be treated functionally and preventatively, include, for example, neurodegenerative disorders such as Parkinson's disease, Alzheimer's disease, Huntington's chorea, amyotrophic lateral sclerosis, and olivopontocerebellar degeneration. According to the invention, the compounds can be used for the prevention of postischemic cellular degeneration, cellular degeneration after brain trauma, in the case of stroke, hypoxia, anoxia and hypoglycemia and for the treatment of senile dementia, AIDS dementia, neurological symptoms that are related to HIV infections, multiinfarct dementia as well as epilepsy and muscle spasms. The psychiatric diseases include anxiety conditions, schizophrenia, migraines, pain conditions as well as the treatment of sleep disorders and withdrawal symptoms after drug abuse such as in alcohol, cocaine, benzodiazepine or opiate withdrawal. In addition, the compounds can be used in the prevention of tolerance development during long-term treatment with sedative pharmaceutical agents, such as, for example, benzodiazepines, barbiturates and morphine. Moreover, the compounds can be used as anesthetics (anesthesia), analgesics or anti-emetics.

For use of the compounds according to the invention as pharmaceutical agents, the latter are brought into the form of a pharmaceutical preparation, which in addition to the active ingredient for enteral or parenteral administration contains suitable pharmaceutical, organic or inorganic inert media, such as, for example, water, gelatin, gum arabic, lactose, starch, magnesium stearate, talc, vegetable oils, polyalkylene-glycols, etc. The pharmaceutical preparations can be present in solid form, for example, as tablets, coated tablets, suppositories, capsules or in liquid form, for example as solutions, suspensions or emulsions. Moreover, they optionally contain adjuvants such as preservatives, stabilizers, wetting agents or emulsifiers, salts for changing the osmotic pressure or buffers.

For parenteral use, especially injection solutions or suspensions, especially aqueous solutions of the active compounds in polyhydroxyethoxylated castor oil, are suitable.

As vehicle systems, surface-active adjuvants such as salts of bile acids or animal or vegetable phospholipids, but also mixtures of them as well as liposomes or their components, can also be used.

For oral use, especially tablets, coated tablets or capsules with talc and/or hydrocarbon vehicles or binders, such as, for example, lactose, corn or potato starch, are suitable. The substance may also be administered in liquid form, such as, for example, as juice, to which optionally a sweetener is added.

The dosage of the active ingredients can vary depending on method of administration, age and weight of the patient, type and severity of the disease to be treated and similar factors. The daily dose is 0.5–1000 mg, preferably 50–200 mg, whereby the dose can be given as a single dose to be administered once or divided into two or more daily doses.

The production of the compounds according to the invention is carried out for example, in that a) a compound of formula II

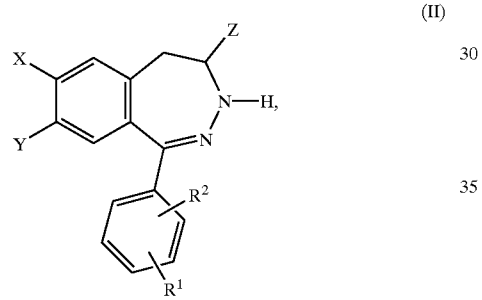

(II)

in which
$R^1$, $R^2$, X and Y have the above meaning, is cyclized by reaction of
α) Z=COOC$_{1-6}$ alkyl with $R^3$—N=C=O to compounds with A meaning —CO—NR$^3$—CO
β) Z=CH$_2$OH or —CH$_2$—NHR$^3$ with phosgene to compounds with A meaning —CH$_2$—O—CO— or —CH$_2$—NR$^3$—CO—;
γ) Z=—CH$_2$OH with $R^3$—CO—$R^4$ to compounds with A meaning —CH$_2$—O—CR$^3$R$^4$, in which $R^3$ and $R^4$ have the above meaning, b) a compound of formula III or IV

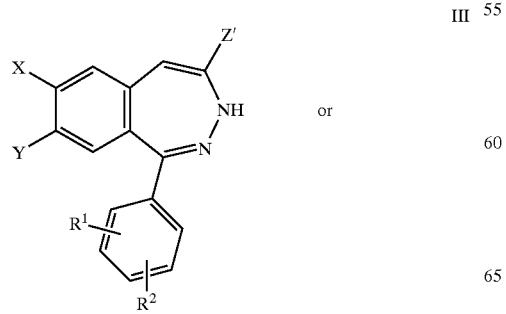

III or

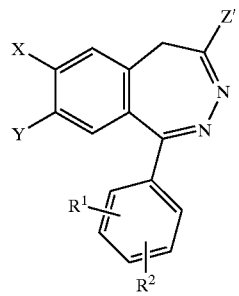

IV in which $R^1$, $R^2$, X and Y have the above meaning, is cyclized by reaction of
α) Z'=—CH=CH—COOC$_{1-6}$ alkyl with borane-trimethylamine complex and boron trifluoride etherate to compounds with A meaning —(CH$_2$)$_3$— and —(CH$_2$)$_2$—CO—.
Z'=—CH=N—NH$^2$ in the presence of copper sulfate to compounds with A meaning =CH—N=N—.
γ) Z'=—S—C$_{1-4}$ alkyl with hydrazine hydrate and acid anhydrides or with acid hydrazides to compounds with A meaning =N—N=CR$^3$—
δ) Z'=—S—C$_{1-4}$ alkyl with α-aminoacetals to compounds with A meaning =N—CR$^3$=CR$^4$—
ε) Z'=CH$_2$OH is converted into CH$_2$NH$_2$, the latter is acylated and cyclized to compounds with A meaning =CH—N=CR$^3$—, c) a compound of formula V,

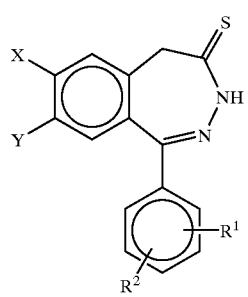

V in which $R^1$, $R^2$, X and Y have the meaning given above, is reacted with α-aminoacetals, α-aminoketals, H$_2$N—CH$_2$≡C—R$^3$ or with ammonia and α-haloketones, and then optionally nitro group $R^1$ and/or $R^2$ is reduced, the amino group is acylated or alkylated or converted into halogen or hydroxy or cyano or deaminated or X is dehalogenated simultaneously with the reduction of the nitro group or in succession or hydrogen is substituted by halogen or halogen is exchanged for another halogen, —PO$_3$R$^{13}$R$^{14}$, cyano, C$_{1-6}$ alkanoyl, C$_{1-6}$ alkanoyloxy, hydroxy, optionally substituted C$_{2-6}$ alkynyl, optionally substituted C$_{2-6}$ alkenyl, optionally substituted C$_{1-6}$ alkyl, C$_{1-6}$ alkoxy, CF$_3$, C$_{1-6}$ thioalkyl, COOR$^{12}$, or Y is re-etherified or the isomers are separated or the salts are formed.

It is advisable to carry out the fusing of the heterocycle on 2,3-benzodiazepines that are suitably substituted in the 4-position.

The reaction of the alkyl radical, in which Z=—COO—C$_{1-6}$ alkyl, with $R^3$—N=C=O in aprotic solvents such as halogenated hydrocarbons at room temperature or a higher temperature results in compounds of formula I with A meaning —CO—NR$^3$—CO—. If compounds of formula II in which Z=—CH$_2$OH or —CH$_2$—NHR$^3$ are reacted with phosgene in the presence of tertiary amines in inert solvents, such as optionally halogenated hydrocarbons, compounds of formula I with A meaning —CH$_2$—O—CO— or —CH$_2$—NR$^3$—CO— are obtained.

If compounds of formula II, in which Z=—CH$_2$OH, are reacted with carbonyl compounds in the presence of acids such as hydrochloric acid, compounds of formula I, in which A means —CH$_2$—O—CR$^3$R$^4$—, are obtained as cyclization products.

If the 2,3-benzodiazepine in the 4-position contains a formyl group, the latter can be converted in, e.g., a Wittig reaction in the usual way into a compound of formula III, in which Z'=—CH=CH—COO—C$_{1-6}$ alkyl.

If the acrylic acid ester that is obtained is treated with borane-trimethylamine complex and with boron trifluoride etherate in a halogenated hydrocarbon such as dichloromethane, compounds of formula I are obtained with A=—(CH$_2$)$_3$— and —(CH$_2$)$_2$—CO—, which can be separated by column chromatography. If the 2,3-benzodiazepine that is formylated in 4-position is reacted with hydrazine hydrate, the corresponding hydrazone derivative, which is dissolved in polar solvents and mixed with a solution of copper sulfate in water, is obtained. Compounds of formula I, in which A means =CH—N=N—, are obtained as cyclization products.

If a compound of formula III or IV, in which Z' means C$_{1-4}$ alkyl-S—, is reacted with acid hydrazides in the presence of an acid, e.g., sulfonic acid in an organic solvent, compounds of formula I, in which A means =N—N=CR$^3$—, are obtained. The reaction can also be performed such that the alkylthio derivative in an organic solvent is heated with hydrazine hydrate, and then is reacted with an acid anhydride to the desired product.

If the methylthio-benzodiazepine derivative is heated with α-aminoacetals H$_2$N—CR$^3$H—CH—(O-alkyl)$_2$, H$_2$N—CH$_2$—CR$^4$—(O-alkyl)$_2$ or H$_2$N—CR$^3$H—CR$^4$—(O-alkyl)$_2$ in the presence of an acid, such as p-toluenesulfonic acid, compounds of formula I with A meaning =N—CR$^3$=CH—, =N—CH=CR$^4$— or =N—CR$^3$=CR$^4$— are obtained.

The same compounds of formula I can be produced by a compound of formula V being reacted with the corresponding α-aminoacetal NH$_2$CHR$^3$—CR$^4$(OAlk)$_2$ optionally in solvents such as Cellosolve$^{(R)}$ by introducing an inert gas, such as, e.g., argon or nitrogen to remove the hydrogen sulfide or in the presence of sulfur catchers, such as, e.g., mercury oxide. Radical (OAlk)$_2$ is defined as either open or else—sometimes more advantageously—cyclic acetals or ketals. Compounds of formula I can also be produced by compounds of formula V being reacted with propargylamines H$_2$N—CH$_2$—C≡CR$^3$ according to processes known in the literature (Eur. J. Med. Chem. 30, 429 (1995) or Ann. Chem. 1987, (2), 103).

Compounds of formula I are obtained even if compounds of formula V with ammonia in solvents such as methanol or Cellosolve$^{(R)}$ optionally are converted under pressure or with the addition of a sulfur catcher, such as, for example, silver triflate or mercury oxide, into the corresponding imine and then reacted with α-haloketones.

If Z' is a CH$_2$OH group, the alcohol can be converted in a known way by reaction according to Mitsunobu into azide or into phthalimide. Azide can be converted into amine according to methods in literature by reducing agents or by triphenylphosphine. Phthalimide can also be converted into amine by treatment with hydrazine. The acylation of this amine is possible with acid chlorides or acid anhydrides according to known processes. The subsequent cyclization with phosphorus oxychloride results in compounds of formula I with A meaning =CH—N=CR$^3$—.

The reduction in the nitro group is performed in polar solvents at room temperature or a higher temperature. As catalysts for reduction, metals such as Raney nickel or noble metal catalysts such as palladium or platinum or else palladium hydroxide optionally on vehicles are suitable. Instead of hydrogen, for example, ammonium formate, cyclohexene or hydrazine can also be used in a known way. Reducing agents such as tin(II) chloride or titanium(III) chloride can also be used as complex metal hydrides optionally in the presence of heavy metal salts. Iron can also be used as a reducing agent. The reaction is then performed in the presence of an acid such as, e.g., acetic acid or ammonium chloride, optionally with the addition of a solvent, such as, for example, water or methanol.

If alkylation of an amino group is desired, it can be performed according to commonly used methods—for example with alkyl halides—or according to the Mitsonubo variant by reaction with an alcohol in the presence of triphenylphosphine and azodicarboxylic acid ester, or the amine can be subjected to reductive amination with aldehydes or ketones optionally in succession with two different carbonyl compounds, whereby mixed derivatives are obtained [Bibliography, e.g., Verardo et al. Synthesis (1993), 121; Synthesis (1991), 447; Kawaguchi, Synthesis (1985), 701; Micovic et al. Synthesis (1991), 1043].

The acylation of an amino group is carried out in the usual way, for example, with an acid halide or acid anhydride optionally in the presence of a base such as dimethylaminopyridine in solvents such as methylene chloride, tetrahydrofuran or pyridine, according to the Schotten-Baumann variant in aqueous solution at weakly alkaline pH or by reaction with an anhydride in glacial acetic acid.

The introduction of the halogens chlorine, bromine or iodine via the amino group can be carried out, for example, also according to Sandmeyer, by the diazonium salts that are intermediately formed with nitrites being reacted with copper(I) chloride or copper(I) bromide in the presence of the corresponding acid such as hydrochloric acid or hydrobromic acid or with potassium iodide. Instead of diazonium salts, the triazenes optionally also can be used. If an organic nitrite is used, the halogen can be introduced into a solvent such as, for example, dimethylformamide, e.g., by addition of methylene iodide or tetrabromomethane. The removal of the amino group can be achieved either by reaction with an organic nitrite in tetrahydrofuran or by diazotization and reductive boiling-down of diazonium salt with, for example, phosphorous acid optionally with addition of copper(I) oxide.

The introduction of fluorine is possible by, for example, Balz Schiemann reaction of diazonium tetrafluoroborate or according to J. Fluor. Chem. 76, 1996, 59–62 by diazotization in the presence of HFx pyridine and subsequent boiling-down optionally in the presence of a fluoride ion source, such as, e.g., tetrabutylammonium fluoride.

The replacement of the amino group by the hydroxy group is carried out according to methods that are known in the literature, preferably by conversion into triazine and subsequent treatment with a strongly acidic ion exchanger (according to Tetr. Letters 1990, 4409).

The introduction of halogens into the annelated ring is carried out according to processes known in the literature, e.g., by reaction with N-bromo- or N-iodosuccinimide in polar solvents, such as tetrahydrofuran, acetonitrile or dimethylformamide or else by reaction with iodic acid and iodine according to Lieb. Ann. Chem. 634, 84, (1960).

The exchange of a halogen in the annelated ring is carried out in a way known in the literature optionally under heavy metal catalysis, for example by palladium(II) or palladium (0) compounds by tin-organic or boron-organic compounds, $C_{2-6}$ alkines, $C_{2-6}$ alkenes, di- or mon-alkylphosphite, cyanide in solvents such as toluene, tetrahydrofuran or dimethylformamide (M. Kosugi et al. Chem. Lett. 7, 1225, 1984). Optionally, a base, such as, e.g., triethylamine or sodium carbonate, and optionally a co-catalyst, such as, e.g., copper (I) iodide, must be added.

Halogens, such as bromine or iodine, can also be reacted with copper salts, such as copper(I) cyanide (introduction of a nitrile group), copper acetate (introduction of an alkanoyloxy group), sodium alcoholate in the presence of copper(I) iodide (introduction of an alkoxy group) or a mixture of copper(I) iodide and sodium trifluoroacetate (introduction of a trifluoromethyl group).

The halogen can also be subjected to a halogen-metal exchange, e.g., by reaction with butyllithium at temperatures of 0° C. to –78° C. in solvents such as ether or tetrahydrofuran optionally with the addition of complexing agents such as tetramethylethylenediamine, and then the halogen can be recovered in a way that is known in the literature with electrophiles, such as, for example, dimethylformamide, alkyl halides such as iodides or chlorides, or aldehydes.

The isomer mixtures can be separated into enantiomers according to commonly used methods, such as, for example, crystallization, chromatography or salt formation.

The production of salts is carried out in the usual way by a solution of the compound of formula I being mixed with the equivalent amount of acid or excess acid, which optionally is in solution, and the precipitate being separated or the solution being worked up in the usual way.

In so far as the production of the starting compounds is not described, the latter are known or can be produced analogously to known compounds.

The invention also comprises the compounds of formulas IIa and IIIa, their isomers and salts

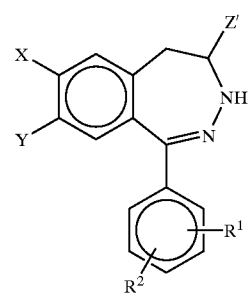

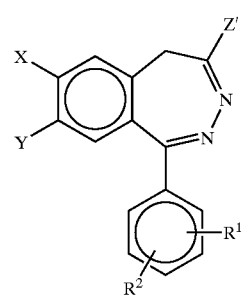

in which
$R^1$, $R^2$, X and Y have the above-indicated meaning and $Z''$ means —$CH_2OH$, —CHO, —COO—$C_{1-6}$alkyl, $CH_2NHR^3$,

and $R^3$ has the above-mentioned meaning, which represent valuable intermediate products for the production of pharmacologically active compounds. The conversion of the intermediate products into active substances is carried out according to the processes described above.

The production of the intermediate products is carried out according to known methods or methods that are described here. If the 2,3-benzodiazepine in the 4-position contains a methyl group, the latter can be oxidized to formyl with, for example, $SeO_2$. Optionally, the formyl group can be reduced to —$CH_2OH$ or oxidized to the carboxyl group, which can then be esterified or the formyl group can be converted into —$CH_2NHR^3$ or subjected to a Wittig reaction.

The following examples are to explain the process according to the invention:

Production of the Starting Compounds

I.)
8-Hydroxymethyl-7-methylcarbamoyl-5-(4-nitrophenyl)-8,9-dihydro-7H-1,3-dioxolo[4,5-h][2,3]benzodiazepine
A. 8-Formyl-5-(4-nitrophenyl)-9H-1,3-dioxolo[4,5-h][2,3]benzodiazepine 1.0 g (3.1 mmol) of 8-methyl-5-(4-nitrophenyl-9H-1,3-dioloxol[4,5-h][2,3]benzodiazepine (French Patent No. 2566774) is dissolved at 90° C. in 15 ml of DMF. 0.38 g (3.4 mmol) of $SeO_2$ is added, and it is stirred for 40 minutes at 90° C. After the solid is filtered off, the product is precipitated with 100 ml of water, the crude product is filtered off, and it is washed with water and dried. 1.04 g of the compound is obtained. After purification by column chromatography (silica gel, eluant benzene/ethyl acetate 20:1)

and subsequent suspension of the crystalline compound in ethanol, 0.52 g (50%) of product is obtained. Melting point 228–230° C. (decomposition).

B. 8-Hydroxymethyl-5-(4-nitrophenyl)-8,9-dihydro-7H-1,3-dioxolo[4,5-h][2,3]-benzodiazepine A suspension of 7.0 g (20.7 mmol) of the aldehyde that is obtained after reaction step A is cooled to 20° C. in 420 ml of ethanol while being stirred and mixed little by little with 7.84 g (0.21 mol) of $NaBH_4$. The reaction mixture is heated to boiling for 1 hour, then mixed with activated carbon and hot-filtered. The solvent is removed, the residue is taken up in dichloromethane, worked up, and 6.37 g (90%) of crude product, which is purified by column chromatography on silica gel with a 1:1 mixture of benzene/ethyl acetate as an eluant, is obtained. 5.46 g (77%) of pure product with melting point 132–134° C. is obtained.

C. 8-Hydroxymethyl-7-methylcarbamoyl-5-(4-nitrophenyl)-8,9-dihydro-7H-1,3-dioxolo[4,5-h][2,3]benzodiazepine 1.0 g (2.9 mmol) of the alcohol that is obtained after reaction step B is dissolved in 40 ml of dichloromethane and mixed with 0.5 ml (8.8 mmol) of methyl isocyanate. The solution is allowed to stand at room temperature for 3 days and then concentrated by evaporation. The crystalline residue is suspended in 10 ml of ethanol and heated to boiling. 1.02 g (87%) of yellow product with a melting point of 242–243° C. (decomposition) is obtained.

II.)

5-(4-Aminophenyl)-8-hydroxymethyl-7-methylcarbamoyl-8,9-dihydro-7H-1,3-dioxolo[4,5-h][2,3]benzodiazepine A suspension of 1.02 g (2.56 mmol) of 8-hydroxymethyl-7-methylcarbamoyl-5-(4-nitrophenyl)-8,9-dihydro-7H-1,3-dioxolo[4,5-h][2,3]benzodiazepine (stage C) in 40 ml of ethanol is mixed with 0.45 ml (9 mmol) of 98% hydrazine hydrate and RaNi catalyst while being stirred. After 30 minutes, the catalyst is filtered off, and the solution is concentrated by evaporation. The residue is recrystallized in ethanol, and 0.83 g (88%) of product with a melting point of 136–138° C. is obtained.

III.)

8-Hydroxymethyl-5-(4-nitrophenyl)-9H-1,3-dioxolo[4,5-h][2,3]benzodiazepine 2.5 g (7.41 mmol) of 8-formyl-5-(4-nitrophenyl)-9H-1,3-dioxolo[4,5-h][2,3]benzodiazepine (I, stage A) is suspended in THF:water=1:1 and mixed with 0.14 g (3.7 mmol) of sodium boranate while being stirred and cooled to 20° C. After 45 minutes of stirring, it is filtered and the crude product is precipitated from the filtrate with 130 ml of water. 2.35 g, which is recrystallized from a mixture of 6.3 ml of dimethylformamide and 1.3 ml of water, is obtained. 1.97 g (78%) of the title compound with a melting point of 175° C. (decomposition) is obtained.

EXAMPLE 1

9-Methyl-5-(4-nitrophenyl)-11H-1,3-dioxolo[4,5-h]imidazo[3,4-c][2,3]benzodiazepine-8,10(9H,10aH)-dione

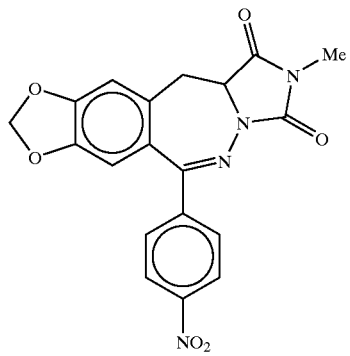

A. 5-(4-Nitrophenyl)-9H-[1,3-]dioxolo[4,5-h][2,3]-benzodiazepine-8-carboxylic acid 42 ml of a 4% NaOH solution is added to a solution of 3.0 g of $AgNO_3$ in water (50 ml). The solution of 3.0 g of 8-formyl-5-(4-nitrophenyl)-9H-1,3-dioxolo[4,5-h-][2,3]-benzodiazepine in 120 ml of dioxane is slowly added to the heterogeneous mixture, and the reaction mixture is stirred for 30 minutes at 25° C. After activated carbon is added, it is filtered, the filtrate is concentrated by evaporation in a vacuum at 50–60° C., the suspension that is produced is diluted with 30 ml of water and cooled. After standing overnight, it is filtered off, the precipitate is washed with 2×10 ml of ice water, and 1.94 g of sodium salt, which is dissolved in 60 ml of hot water and, after cooling, acidified with 1 ml of acetic acid, is obtained. After filtration and washing with water, 1.66 g (53%) of product with a melting point of 196–198° C. (decomposition) is obtained.

B. 8-(Methoxycarbonyl)-5-(4-nitrophenyl)-9H-1,3-dioxolo[4,5-h][2,3]benzodiazepine 8.0 g (22.0 mmol) of the compound that is obtained after reaction step A is suspended in 390 ml of methanol and, after 4.2 ml (34.4 mmol) of boron trifluoride etherate is added, the mixture is refluxed for 3 hours. The solvent is drawn off, the residue is taken up in dichloromethane and 100 ml of a 10% $Na_2CO_3$ solution, and it is stirred for 30 minutes. The crude product that is obtained after working-up[1] is purified by column chromatography (silica gel, eluant: benzene/ethyl acetate 20:1), and 3.86 g (46%) of the title compound with a melting point of 235–238° C. (decomposition) is obtained.

[1]Here and in the other examples, working up is defined as: The organic phase is washed with water, dried, filtered and concentrated by evaporation.

C. 8-(Methoxycarbonyl)-5-(4-nitrophenyl)-8,9-dihydro-7H-1,3-dioxolo[4,5-h][2,3]-benzodiazepine A suspension of 2.94 g (8.0 mmol) of the compound that is obtained after reaction step B in 30 ml of dichloromethane is mixed with 15 ml of trifluoroacetic acid while being stirred. 6.3 ml (40 mmol) of triethylsilane is added and stirred for 24 hours at room temperature. Then, it is mixed with 30 ml of dichloromethane, and a solution of 12.3 g of $Na_2CO_3$ in 60 ml of water is added while being stirred and cooled with ice water. The residue that is obtained after working-up is treated with 20 ml of methanol, and 2.85 g (96%) of the title compound with a melting point of 161–164° C. is obtained.

D. 9-Methyl-5-(4-nitrophenyl)-11H-1,3-dioxolo[4,5-h]imidazo[3.4-c][2,3]benzodiazepine-8,10(9H,10aH)-dione 0.85 g (2.3 mmol) of the compound that is obtained after reaction step C is dissolved in 30 ml of dichloromethane, and it is allowed to react for 3 weeks at room temperature with 1.0 ml (17.5 mmol) of methyl isocyanate. The solvent is drawn off, and the residue is purified by boiling with methanol. After suctioning-off, 0.77 g (84%) of the product with a melting point of 242–244° C. (decomposition) is obtained.

EXAMPLE 2

5-(4-Aminophenyl)-9-methyl-11H-1,3-dioxolo[4,5-h]imidazo[3,4-c][2,3]benzodiazepine-8,10(9H,10aH)-dione

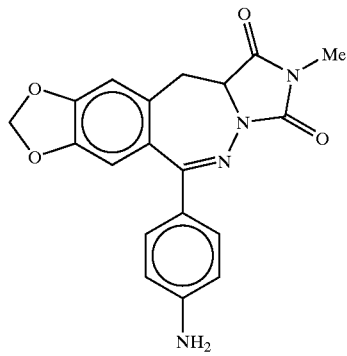

0.61 g (1.55 mmol) of the nitro compound that is obtained according to Example 1 is reduced with RaNi/hydrazine hydrate in a 2:1 mixture of dichloromethane/methanol. The catalyst is filtered off, the solution is concentrated by evaporation, the crystalline residue is washed with water, and 0.54 g (54%) of the title compound with a melting point >270° C. (decomposition) is obtained.

EXAMPLE 3

9-Methyl-5-(4-nitrophenyl)-9,10,10a,11-tetrahydro-8H-1,3-dioxolo[4,5-i]imidazo[3,4-c][2,3]benzodiazepin-8-one

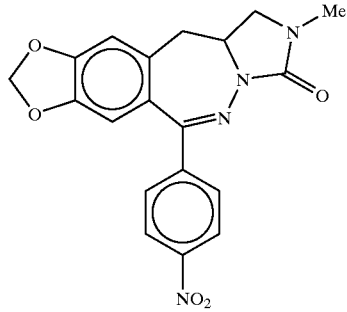

A. 8-[(Methylimino)methyl]-5-(4-nitrophenyl)-9H-1,3-dioxolo[4,5-h][2,3]benzodiazepine 2.0 g (5.9 mmol) of 8-formyl-5-(4-nitrophenyl)-9H-1,3-dioxolo[4,5-h][2,3]benzodiazepine is dissolved in 100 ml of a 1:1 mixture of dichloromethane-methanol, mixed with 40 ml of a 33% solution of methylamine in ethanol and allowed to stand for 24 hours at room temperature. Then, the solvent is drawn off, and the residue is boiled with 25 ml of ethanol. After filtration, 1.95 g (93%) of the title compound with a melting point of 245–247° C. (decomposition) is obtained.

B. 5.5 g (15.7 mmol) of the imine that is obtained after reaction step A is suspended in 800 ml of ethanol and mixed in portions with 26 ml of concentrated HCl while being stirred. 13.6 g (0.36 mmol) of $NaBH_4$ is added to the solution that is obtained for 1 hour in small portions. It is stirred for 30 more minutes, filtered, the filtrate is concentrated by evaporation and the residue is purified by column chromatography with methanol as an eluant. 3.67 g (66%) of 8-[(methylamino)methyl]-5-(4-nitrophenyl)-9H-1,3-dioxolo[4,5-h][2,3]benzodiazepine with a melting point of 110–112° C. is obtained.

C. 9-Methyl-5-(4-nitrophenyl)-9,10,10a, 11-tetrahydro-8H-1,3-dioxolo[4,5-h]imidazo[3,4-c][2,3]benzodiazepin-8-one 2.26 ml (3.6 mmol) of a 15.6% phosgene solution in toluene is added drop by drop to a cooled and stirred solution of 1.05 g (3.0 mmol) of the methylaminomethyl compound after reaction step B and 0.99 ml (7.2 mmol) of triethylamine in 15 ml of dichloromethane. The mixture is stirred for 2 hours and evaporated to the dry state. The residue is treated with water, and 1.08 g of crude product, which is purified by boiling in 10 ml of ethanol, is obtained. After suctioning-off, 0.96 g (84%) of the title compound with a melting point of 252–255° C. is obtained.

EXAMPLE 4

5-(4-Aminophenyl)-9-methyl-9,10,10a, 11-tetrahydro-8H-1,3-dioxolo[4,5-h]imidazo[3,4-c][2,3]benzodiazepin-8-one

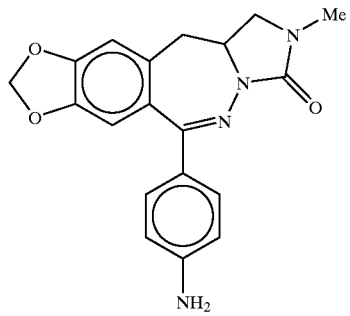

0.38 g (1.0 mmol) of the nitro compound of Example 3 is reduced in 20 ml of methanol with RaNi and hydrazine hydrate analogously to Example 2. After boiling with ethanol, 0.25 g (71%) of the title compound of ethanol with a melting point of 280–289° C. (decomposition) is obtained.

EXAMPLE 5

5-(4-Nitrophenyl)-9,10,10a, 11-tetrahydro-8H-1,3-dioxolo[4,5-h]pyrrolo[2-c][2,3]benzodiazepine

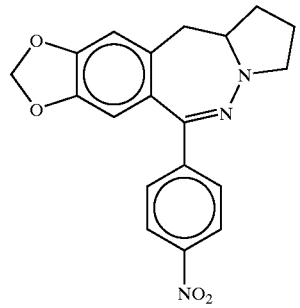

A.

Methyl-3-[5-(4-nitrophenyl)-9H-1,3-dioxolo[4,5-h][2,3]benzodiazepin-8-yl]-propenolate 1.9 ml (13.6 mmol) of triethylamine and 5.64 g (13.6 mmol) of methoxycarbonylmethyl-triphenylphosphonium bromide are added in succession to a solution of 4.0 g (11.8 mmol) of 8-formyl-5-(4-nitrophenyl)-9H-1,3-dioxolo[4,5-h][2,3]benzodiazepine in 200 ml of a 1:1 mixture of dichloromethane and methanol while being stirred. After 2 hours at room temperature, the solvent is drawn off from the suspension, the residue is suspended in 70 ml of ethanol and filtered. After washing three times each with 10 ml of ethanol and 50 ml of water and subsequent drying of the suctioned-off solid, 4.44 g (95%) of methyl-3-[5-(4-nitrophenyl)-9H-1,3-dioxolo[4,5-h][2,3]benzodiazepin-8-yl]-propenolate with a melting point >260° C. is obtained.

B.

5-(4-Nitrophenyl)-9,10,10a,11-tetrahydro-8H-1,3-dioxolo[4,5-h]pyrrolo[1,2-c][2,3]benzodiazenine 2.22 g (30.4 mmol) of borane-trimethylamine complex is added to the suspension of 9.0 g (22.9 mmol) of the compound that is obtained after stage A in dry dichloromethane (660 ml), and 5.0 ml (40.6 mmol) of boron trifluoride etherate is added drop by drop while being stirred vigorously. After it was stirred overnight, it is mixed with 300 ml of 10% Na$_2$CO$_3$ solution, the organic phase is separated and worked up in the usual way. The residue is purified by column chromatography (silica gel, eluant benzene:ethyl acetate=4:0.5). 0.72 g (9%) of the title compound with a melting point of 170–172° C. (decomposition) is obtained.

EXAMPLE 6

5-(4-Nitrophenyl)-9,10,10a,11-tetrahydro-8H-1,3-dioxolo[4,5-h]pyrrolo[2-c][2,3]benzodiazepin[4,5-h]8-one

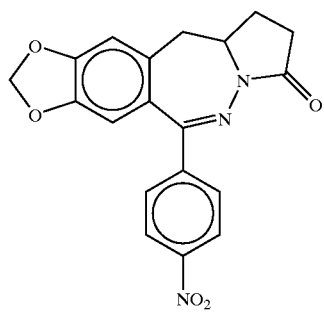

If the crude product that is obtained according to Example 5 is chromatographed on silica gel with the more polar mixture of ethyl acetate:benzene=4:1 as an eluant, 1.26 g (15%) of the title compound with a melting point of 251–253° C. (decomposition) is obtained.

EXAMPLE 7

5-(4-Aminophenyl)-9,10,10a,11-tetrahydro-8H-1,3-dioxolo[4,5-h]pyrrolo[2-c][2,3]benzodiazepine

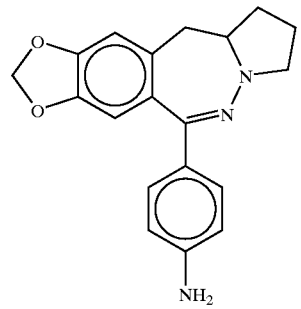

0.68 g (1.94) mmol of the nitro compound according to Example 5 is reduced in methanol with RaNi/hydrazine hydrate analogously to Example 2. After recrystallization from a mixture of 50% ethanol/water, 0.48 g (77%) of the title compound with a melting point of 153–155° C. is obtained.

EXAMPLE 8

5-(4-Nitrophenyl)-9,10,10a,11-tetrahydro-8H-1,3-dioxolo[4,5-h]pyrrolo[1,2-c][2,3]benzodiazepin[4,5-h]8-one

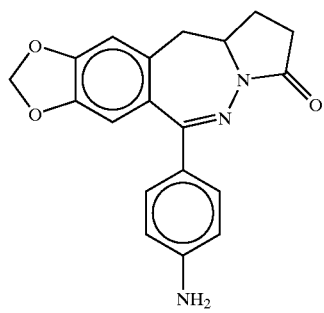

The compound that is obtained according to Example 6 is reduced in 1:1 dichloromethane/methanol RaNi/hydrazine

EXAMPLE 9

5-(4-Nitrophenyl)-11H-1,3-dioxolo[4,5-i][1,2,3]triazolo[4,3-c][2,3]benzodiazepine

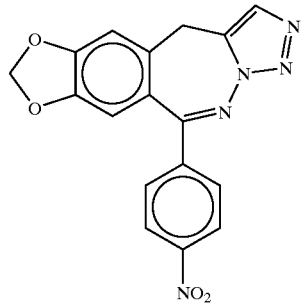

A.

8-Formyl-5-(4-nitrophenyl)-9H-1,3-dioxolo[4,5-h][2,3]benzodiazepine-hydrazone 3.0 g (8.9 mmol) of 8-formyl-4-(4-nitrophenyl)-9H-1,3-dioxolo[4,5-h][2,3]benzodiazepine is suspended in 18 ml of DMF and mixed with 1.3 ml (26.7 mmol) of 98% hydrazine hydrate and heated for 1 hour to 110–120° C. After cooling to room temperature, it is added to water, suctioned off, and the residue is washed with water and dried. This crude product is 80% recrystallized from DMF-water. 2.51 g (80%) of the title compound with a melting point of 221–223° C. (decomposition) is obtained.

B.

5-(4-Nitrophenyl)-11H-1,3-dioxolo[4,5-i][1,2,3]triazolo[4,3-c][2,3]benzodiazepine 2.0 g (5.7 mmol) of the compound that is obtained after process step A is dissolved while being heated slightly in 1:1 THF-methanol and mixed with a solution of 7.0 g of CuSO$_4$·5H$_2$O in 190 ml of water while being stirred. After 30 minutes, the organic solvent is removed, and the residue is dissolved in chloroform and water. The organic phase is separated, washed with water, dried and concentrated by evaporation. After recrystallization from a 10:1 mixture of DMF and water, 1.33 g (67%) of the title compound with a melting point of 257–258° C. (decomposition) is obtained.

hydrate analogously to Example 2. After recrystallization from ethanol, 0.8 g (80%) of the title compound with a melting point of 291–292° C. (decomposition) is obtained.

EXAMPLE 10

5-(4-Aminophenyl)-11H-1,3-dioxolo[4,5-i][1,2,3]triazolo[4,3-c][2,3]benzodiazepine

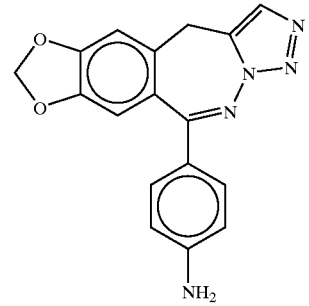

1.17 g (3.35 mmol) of the nitro compound of Example 9 is reduced in 100 ml of a 1:1 mixture of dichloromethane-methanol with RaNi/hydrazine hydrate analogously to Example 2. After recrystallization from DMF-water (10:1), 0.8 g (74%) of the title compound with a melting point >260° C. (decomposition) is obtained.

EXAMPLE 11

10a,11-Dihydro-8,8-dimethyl-5-(4-nitrophenyl)-10H-1,3-dioxolo[4,5-h]oxazolo-[3,4-c][2,3]benzodiazepine

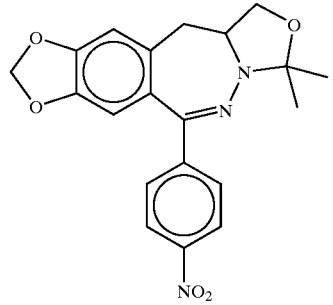

1.87 g (5.48 mmol) of 8-hydroxymethyl-5-(4-nitrophenyl)-8,9-dihydro-7H-1,3-dioxolo[4,5-h][2,3]benzodiazepine is dissolved in 25 ml of acetone and mixed with 0.54 ml (6.67 mmol) of 37% HCl. After 30 minutes, the reaction mixture is cooled, and the hydrochloride is filtered off. The dichloromethane suspension of this salt is shaken with 20 ml of 8% NaHCO$_3$ solution until the salt is dissolved. The organic phase is separated, washed with water, dried and concentrated by evaporation. After recrystallization, 1.7 g (81%) of the title compound, melting point 171–173° C., is obtained.

EXAMPLE 12

5-(4-Aminophenyl)-10a, 11-dihydro-8,8-dimethyl-10H-1,3-dioxolo[4,5-h]oxazolo-[3,4-c][2,3]benzodiazepine

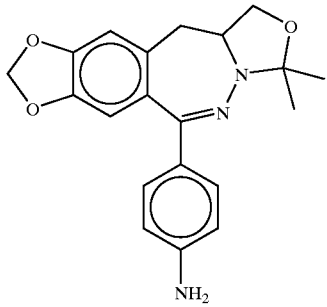

Analogously to Example 2, 1.2 g (76%) of the title compound with a melting point of 133–135° C. (ethanol:water=1:1) is obtained from 1.7 g (4.46 mmol) of the compound of Example 11 with RaNi/hydrazine hydrate in methanol.

EXAMPLE 13

10a, 11-Dihydro-5-(4-nitrophenyl)-10H-1,3-dioxolo[4,5-h]oxazolo-[3,4-c][2,3]benzodiazepin-8-one

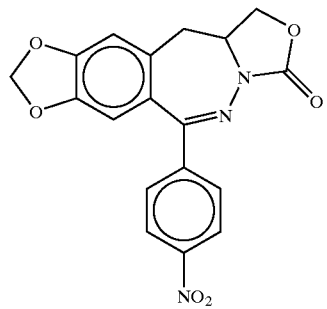

A solution of 1.0 g (2.93 mmol) of 8-hydroxymethyl-5-(4-nitrophenyl)-8,9-dihydro-7H-1,3-dioxolo[4,5-h][2,3]-benzodiazepine is mixed in succession with 0.98 ml (7.03 mmol) of triethylamine and 2.23 ml (3.52 mmol) of a 15.6% phosgene solution in toluene while being stirred and cooled. Then, the reaction mixture is heated for 3 hours to 25° C. The precipitate of the crude product is separated, the filtrate is concentrated by evaporation and the residue is treated with water. The combined residues are boiled with ethanol, and after suctioning-off, 0.72 g (67%) of the title compound with a melting point >250° C. (decomposition) is obtained.

EXAMPLE 14

5-(4-Aminophenyl-10a,11-dihydro-10H-1,3-dioxolo[4,5-h]oxazolo-[3,4-c][2,3]benzodiazepin-8-one

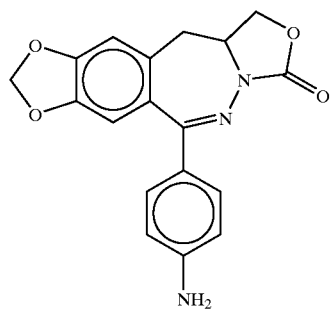

0.5 g (1.36 mmol) of the nitro compound that is obtained according to Example 13 is reduced in DMF with RaNi/hydrazine hydrate analogously to Example 2. The crude product is purified in 4.5 ml of hot ethanol, and 0.49 g (85%) of the title compound with a melting point of 173–175° C. is obtained.

EXAMPLE 15

5-(4-Nitrophenyl)-8-methyl-11H-1,3-dioxolo[4,5-h][1,2,4]triazolo[4,3-c][2,3]benzodiazepine

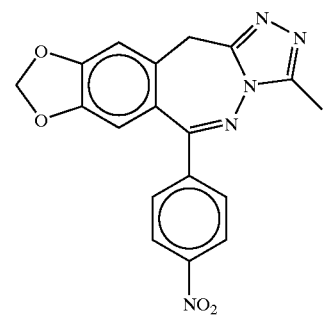

A.
5-(4-Nitrophenyl)-1,3-dioxolo[4,5-g]-isochroman 36.0 g (0.21 mmol) of 2-(1,3-benzodioxol-5-yl)-ethanol is reacted with an equivalent amount of 4-nitrobenzaldehyde analogously to C.A. 105, 1986, 226357, and 50.7 g (81%) of the title compound, melting point 149–150° C. (ethanol), is obtained.

B.
4,5-Methylenedioxy-2-(4-nitrobenzoyl)-phenylacetic acid 10.0 g (33.4 mmol) of the isochroman that is obtained after reaction step A is oxidized to the title compound according to Jones (F. Gatta et al. Il Farmaco 40, 1985, 942–955), yield 46%, melting point 237–239° C. (Methyl Cellosolve®).

C.
5-(4-Nitrophenyl)-7H-1,3-dioxolo[4,5-h][2,3]benzodiazepin-8(9H)-one 5.0 g (15.2 mmol) of the compound that is obtained after reaction step B is reacted in Methyl Cellosolve® (50 ml) at 110° C. with 5.0 ml of 98% hydrazine hydrate for 2.5 hours. The solvent is drawn off in a vacuum, and the residue is dissolved in dichloromethane (200 ml) and 40% acetic acid (20 ml). The organic phase is separated, washed with water and dried. 4.0 g (19.4 mmol) of 1,3-dicyclohexylcarbodiimide is added and allowed to stand overnight at room temperature. The precipitate is filtered off, and the filtrate is concentrated by evaporation. Both solids are heated with 60 ml of ethanol and then suctioned off. 1.95 g (39%) of the title compound, melting point 292–294° C., is obtained.

D. 5-(4-Nitrophenyl)-7H-1,3-dioxolo[4,5-h][2,3]benzodiazepin-8(9H)-thione 6.5 g (20.0 mmol) of the compound that is obtained after reaction step C and 7.6 g (30.0 mmol) of phosphorus pentasulfide are heated in 100 ml of pyridine to 80° C. After 1.5 hours, the reaction mixture is poured into 400 ml of water, and the pH of the solution is set at 6.5 with acetic acid. The precipitate is filtered off, washed and dried. 4.36 g (64%) of product, melting point 257–258° C. (acetone), is obtained.

Produced analogously via stages A–D are:
5-(4-Chlorophenyl)-7H-1,3-dioxolo[4,5-h][2,3]benzodiazepine-8(9H)-thione
5-(4-fluorophenyl)-7H-1,3-dioxolo[4,5-h][2,3]benzodiazepine-8(9H)-thione
5-(2-fluorophenyl)-7H-1,3-dioxolo[4,5-h][2,3]benzodiazepine-8(9H)-thione
5-(3-chlorophenyl)-7H-1,3-dioxolo[4,5-h][2,3]benzodiazepine-8(9H)-thione
5-(2-chlorophenyl)-7H-1,3-dioxolo[4,5-h][2,3]benzodiazepine-8(9H)-thione
5-phenyl-7H-1,3-dioxolo[4,5-h][2,3]benzodiazepine-8(9H)-thione E. 8-(Methylthio)-5-(4-nitrophenyl)-9H-1,3-dioxolo-[4,5-h][2,3]benzodiazepine 2.2 g (6.45 mmol) of the compound that is obtained after reaction step D is dissolved in 500 ml of acetone and mixed with 2.22 g of $K_2CO_3$ and 2 ml (32 mmol) of methyl iodide. It is stirred for about 2 days, poured into water, the precipitate is separated, and it is washed with water. After drying, 2.0 g (87%) of product, melting point 280–281° C., is obtained.

Produced analogously are:
5-(2-Fluorophenyl)-8-(methylthio)-9H-1,3-dioxolo-[4,5-h][2,3]benzodiazepine
5-(3-chlorophenyl)-8-(methylthio)-9H-1,3-dioxolo-[4,5-h][2,3]benzodiazepine
5-(2-chlorophenyl)-8-(methylthio)-9H-1,3-dioxolo-[4,5-h][2,3]benzodiazepine
8-(methylthio)-5-phenyl-9H-1,3-dioxolo-[4,5-h][2,3]benzodiazepine F. 5-(4-Nitrophenyl)-8-methyl-11H-1,3-dioxolo[4,5-h][2,4]triazolo[4,3-c][2,3]benzodiazepine 0.53 g (1.50 mmol) of the compound that is obtained after reaction step E, 0.22 g (3.0 mmol) of acetic acid hydrazide, and 0.1 g of p-toluenesulfonic acid are heated to 120° C. in 25 ml of Methyl Cellosolve® while being stirred. After 45 minutes, the reaction mixture is poured into water, the precipitate is separated, washed with water and dried. 0.45 g (83%) of product, melting point 292–294° C. (decomposition), is obtained.

EXAMPLE 16

5-(4-Aminophenyl)-8-methyl-11H-1,3-dioxolo[4,5-h][2,4]triazolo[4,3-c][2,3]benzodiazepine

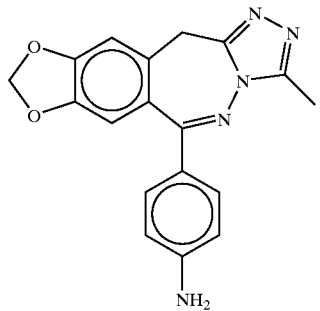

0.45 g of the nitro compound that is obtained according to Example 15 is reduced in methanol with RaNi/hydrazine hydrate analogously to Example 2, and 0.40 g (97%) of product, melting point 278–280° C. (ethanol), is obtained.

EXAMPLE 17

5-(4-Nitrophenyl)-8-ethyl-11H-1,3-dioxolo[4,5-h][2,4]triazolo[4,3-c][2,3]benzodiazenine

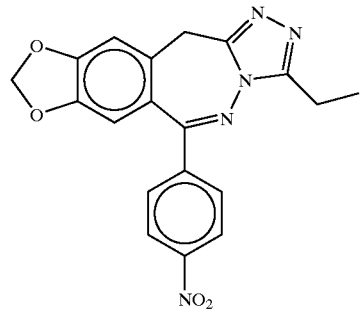

Analogously to Example 15, the product is obtained with propionic acid hydrazide after process step F. Yield 71%, melting point 234–235° C.

Produced in a basically similar way are:
5-(4-Nitrophenyl)-8-propyl-11H-1,3-dioxolo[4,5-h][1,2,4]triazolo[4,3-c][2,3]benzodiazepine (melting point 124–126° C.)
5-(4-nitrophenyl)-8-cyclopropyl-11H-1,3-dioxolo[4,5-h][1,2,4]triazolo[4,3-c][2,3]benzodiazepine (melting point 154–156° C.)
5-(4-nitrophenyl)-8-n-butyl-11H-1,3-dioxolo[4,5-h][1,2,4]triazolo[4,3-c][2,3]benzodiazepine (melting point 124–125° C.)
5-(4-nitrophenyl)-8-methoxymethyl-11H-1,3-dioxolo[4,5-h][1,2,4]triazolo[4,3-c][2,3]benzodiazepine (melting point 142–143° C.)
5-(2-chlorophenyl)-8-methyl-11H-1,3-dioxolo[4,5-h][1,2,4]triazolo[4,3-c][2,3]benzodiazepine
5-(3-chlorophenyl)-8-(methyl)-11H-1,3-dioxolo[4,5-h][1,2,4]triazolo[4,3-c][2,3]benzodiazepine
5-(2-fluorophenyl)-8-(methyl)-11H-1,3-dioxolo[4,5-h][1,2,4]triazolo[4,3-c][2,3]benzodiazepine
8-methyl-5-phenyl-11H-1,3-dioxolo[4,5-h][1,2,4]triazolo[4,3-c][2,3]benzodiazepine 8-ethyl-5-phenyl-11H-1,3-dioxolo[4,5-h][1,2,4]triazolo[4,3-c][2,3]benzodiazepine
8-cyclopropyl-5-phenyl-11H-1,3-dioxolo[4,5-h][1,2,4]triazolo[4,3-c][2,3]benzodiazepine
8-(4-nitrophenyl)-5-phenyl-11H-1,3-dioxolo[4,5-h][1,2,4]triazolo[4,3-c][2,3]benzodiazepine

EXAMPLE 18

5-(4-Aminophenyl)-8-ethyl-11H-1,3-dioxolo[4,5-h][1,2,4]triazolo[4,3-c][2,3]benzodiazepine

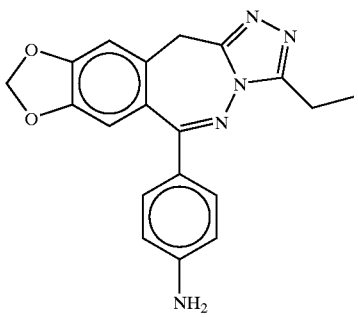

The nitro compound that is obtained according to Example 17 is reduced analogously to Example 16. Yield 84%, melting point 265–266° C. (ethanol).

Produced analogously are:
5-(4-Aminophenyl)-8-propyl-11H-1,3-dioxolo[4,5-h][1,2,4]triazolo[4,3-c][2,3]benzodiazepine (melting point 202–203° C., ethyl acetate)
5-(4-aminophenyl)-8-cyclopropyl-11H-1,3-dioxolo[4,5-h][1,2,4]triazolo[4,3-c][2,3]benzodiazepine (melting point 191–192° C., ethyl acetate/diethyl ether)
5-(4-aminophenyl)-8-n-butyl-11H-1,3-dioxolo[4,5-h][1,2,4]triazolo[4,3-c][2,3]benzodiazepine (melting point 186–187° C., ethyl acetate)
5-(4-aminophenyl)-8-methoxymethyl-11H-1,3-dioxolo[4,5-h][1,2,4]triazolo[4,3-c][2,3]benzodiazepine (melting point 261–263° C., ethanol)
8-(4-aminophenyl)-5-phenyl-11H-1,3-dioxolo[4,5-h][1,2,4]triazolo[4,3-c][2,3]benzodiazepine

EXAMPLE 19

5-(4-Nitrophenyl)-8-(4-pyridyl)-11H-1,3-dioxolo[4,5-h][2,4]triazolo[4,3-c][2,3]benzodiazepine

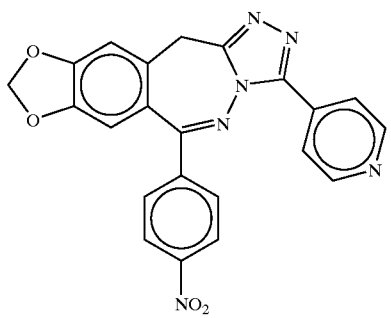

The methylthio derivative that is described in Example 15E is reacted analogously to Example 15F with isonicotinic acid hydrazide in DMF and concentrated hydrochloric acid as a catalyst. Yield 76%, melting point 305–308° C. (decomposition).

Produced analogously is:
5-Phenyl-8-(4-pyridyl)-11H-1,3-dioxolo[4,5-h][1,2,4]triazolo[4,3-c][2,3]benzodiazepine

EXAMPLE 20

5-(4-Aminophenyl)-8-(4-pyridyl)-11H-1,3-dioxolo[4,5-h][1,2,4]triazolo[4,3-c][2,3]benzodiazepine

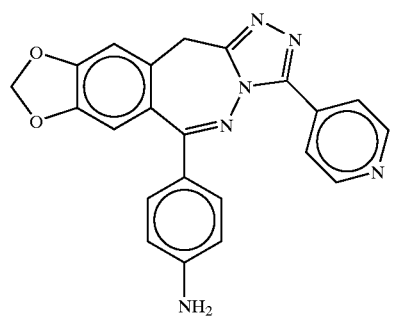

The nitro compound of Example 19 is reduced analogously to Example 2. Yield 46%, melting point 301–302° C. (decomposition).

EXAMPLE 21

5-(4-Nitrophenyl)-11H-1,3-dioxolo[4,5-h][1,2,4]triazolo[4,3-c][2,3]benzodiazepine

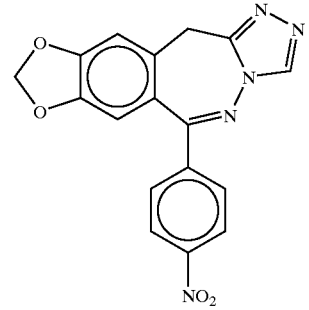

0.53 g of the methylthio compound that is obtained according to Example 15E is reacted analogously to Example 15F with 0.18 g of formic acid hydrazide in DMF with concentrated HCl as a catalyst. After chromatography on silica gel with chloroform:methanol=95:5 as an eluant, 0.34 g (71%) of product is obtained. Melting point 182–183° C.

Produced analogously is:
5-Phenyl-11H-1,3-dioxolo[4,5-h][1,2,4]triazolo[4,3-c][2,3]benzodiazepine

EXAMPLE 22

5-(4-Aminophenyl)-11H-1,3-dioxolo[4,5-][2,4]triazolo[4,3-c][2,3]benzodiazepine

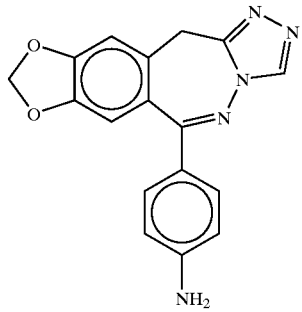

The nitro compound that is obtained according to Example 21 is reduced analogously to Example 2. Yield 70%. Melting point 280–281° C. (ethanol).

EXAMPLE 23

5-(4-Nitrophenyl)-8-(trifluoromethyl)-11H-1,3-dioxolo[4,5-h][2,4]triazolo[4,3-c][2,3]benzodiazepine

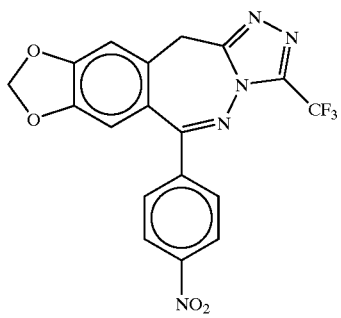

0.53 g (1.50 mmol) of the methylthio compound that is obtained in Example 15E is heated to boiling with 1.5 ml of hydrazine hydrate in 25 ml of Methyl Cellosolve®. After 1 hour, the solvent is drawn off, the residue is taken up in water and the precipitate is filtered off. After drying, the compound is dissolved in dichloromethane, and it is mixed drop by drop with 0.40 ml of trifluoroacetic acid anhydride while being stirred and cooled with ice water. The reaction mixture is then heated to boiling for 1 hour and then evaporated to the dry state. The residue is taken up in toluene, heated for 20 minutes, and the solvent is then removed. After chromatography on silica gel with chloroform:methanol=95:5 as an eluant, 0.27 g (43%) of product is obtained. Melting point 244–246° C. (methanol).

Produced analogously is:

5-Phenyl-8-(trifluoromethyl)-11H-1,3-dioxolo[4,5-h][1,2,4]triazolo[4,3-c][2,3]benzodiazepine

EXAMPLE 24

5-(4-Aminophenyl)-8-(trifluoromethyl)-11H-1,3-dioxolo[4,5-h][1,2,4]triazolo[4,3-c][2,3]benzodiazepine

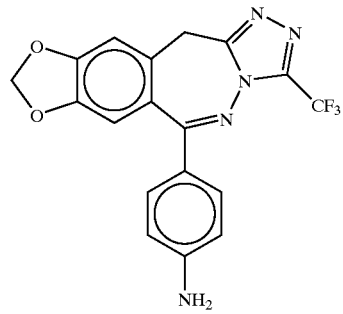

The nitro compound that is obtained according to Example 23 is reduced analogously to Example 2. Yield 68%, melting point 206–208° C. (methanol).

EXAMPLE 25

5-(4-Nitrophenyl)-11H-1,3-dioxolo[4,5-h]imidazo[1,2-c][2.3]benzodiazepine

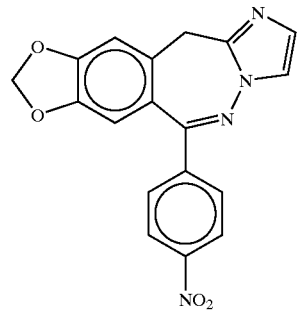

0.53 g (1.50 mmol) of the methylthio derivative that is obtained in Example 15E is heated to 120° C. with 0.10 g of p-toluenesulfonic acid and 0.32 g (3.00 mmol) of aminoacetate aldehyde dimethylacetal. After 10 hours, the reaction mixture is poured into water, and the precipitated intermediate compound is filtered off. This compound is dissolved in 20 ml of a 1:1 mixture of concentrated HCl and ethanol and heated to boiling for 4 hours. After cooling, the hydrochloride of the title compound is obtained by filtration. Yield 0.32 g (55%), melting point 237–239° C.

Produced in a basically similar way is:

5-Phenyl-11H-1,3-dioxolo[4,5-h]imidazo[1,2-c][2,3]benzodiazepine

EXAMPLE 26

5-(4-Aminophenyl)-11H-13-dioxolo[4,5-h]imidazo[1,2-c][2.3]benzodiazepine

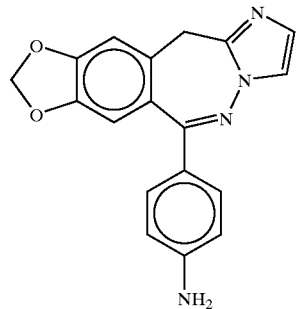

The nitro compound that is produced in Example 25 is reduced analogously to Example 2. Yield 0.2 g (76%), melting point 264–265° C. (ethanol).

EXAMPLE 27

6-(4-Aminophenyl)-8-methoxy-3-propyl-11H-[1,2,4]triazolo[4,3-c][2,3]benzodiazepine

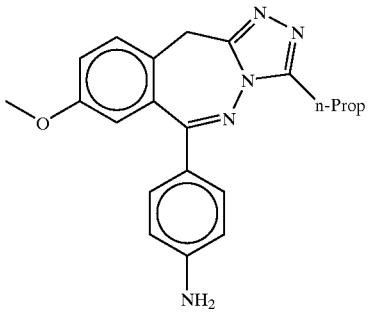

A.

3.90 g (10.0 mmol) of 7-bromo-8-methoxy-1-(4-nitrophenyl)-4,5-dihydro-3H-2,3-benzodiazepin-4-one is dissolved in anhydrous pyridine and mixed with 5.70 g (25.6 mmol) of phosphorus pentasulfide. After 2 hours at 80° C., the mixture is poured onto 450 g of ice and stirred for 1 hour. The precipitated crystals are filtered and washed with water. After recrystallization from acetonitrile, 2.88 g (71%) of 7-bromo-8-methoxy-1-(4-nitrophenyl)-4,5-dihydro-3H-2,3-benzodiazepine-4-thione with a melting point of 245–247° C. is obtained.

B.

2.84 g (7.0 mmol) of the compound of step A is dissolved in 10 ml of anhydrous DMF and 100 ml of acetone, and after 1.93 g (14.0 mmol) of potassium carbonate and 1.75 ml (28.0 mmol) of methyl iodide are added, the mixture is stirred for 20 hours at room temperature. The acetone is then drawn off, and the residue is taken up in 80 ml of water. The precipitated crystals are suctioned off and washed with water. The crude product is recrystallized twice from acetonitrile. 1.68 g (57%) of 7-bromo-8-methoxy-4-methylthio-1-(4-nitrophenyl)-5H-2,3-benzodiazepine with a melting point of 225–227° C. is obtained.

C.

1.17 g (2.78 mmol) of the compound of step B is dissolved in 40 ml of anhydrous DMF and mixed with 0.73 g (8.4 mmol) of butyric acid hydrazide as well as 3 drops of concentrated HCl. The mixture is stirred for 5 hours at 110–115° C. Then, the mixture is poured onto ice (160 g) and stirred for 1 more hour. The precipitated crystals are suctioned off and washed with water. 1.05 g (83%) of 9-bromo-6-(4-nitrophenyl)-8-methoxy-3-propyl-11H-[1,2,4]triazolo[4,3-c][2,3]benzodiazepine with a melting point of 238–240° C. is obtained.

8-Methoxy-3-methyl-6-(4-nitrophenyl)-11H-[1,2,4]triazolo[4,3-c][2,3]benzodiazepine
3-ethyl-8-methoxy-6-(4-nitrophenyl)-11H-[1,2,4]triazolo[4,3-c][2,3]benzodiazepine
3-cyclopropyl-8-methoxy-6-(4-nitrophenyl)-11H-[1,2,4]triazolo[4,3-c][2,3]benzodiazepine

D.

1.0 g (2.2 mmol) of the compound of step C is dissolved in a mixture of 80 ml of methanol and 3 ml of water, and after 0.8 g of 10% Pd/C catalyst and 0.30 g (2.2 mmol) of potassium carbonate are added, it is hydrogenated for about 15 hours. Then, catalyst is suctioned out, and the filtrate is concentrated by evaporation. The crude product is recrystallized from ethyl acetate (3 ml), and 0.44 g (58%) of 6-(4-aminophenyl)-8-methoxy-3-propyl-11H-[1,2,4]triazolo[4,3-c][2,3]benzodiazepine with a melting point of 192–194° C. is obtained.

Produced in a basically similar way are:
6-(4-Aminophenyl)-8-methoxy-3-methyl-11H-[1,2,4]triazolo[4,3-c][2,3]benzodiazepine
6-(4-aminophenyl)-8-methoxy-3-ethyl-11H-[1,2,4]triazolo[4,3-c][2,3]benzodiazepine
6-(4-aminophenyl)-8-methoxy-3-cyclopropyl-11H-[1,2,4]triazolo[4,3-c][2,3]benzodiazepine

EXAMPLE 28

6-(4-Aminophenyl)-8-methoxy-3-methyl-11H-imidazole[1,2-c][2,3]-benzodiazepine

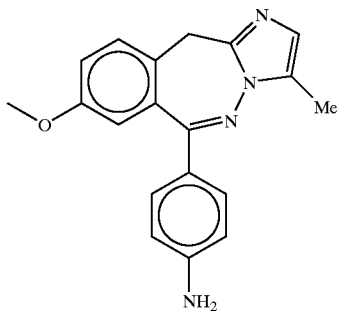

From 9-bromo-8-methoxy-3-methyl-6-(4-nitrophenyl)-11H-imidazo[1,2-c][2,3]benzodiazepine analogously to Example 27D Melting point 190–193° C. (ethyl acetate).

Produced in a basically similar way are:
6-(4-Aminophenyl)-8-methoxy-2-methyl-11H-imidazo[1,2-c][2,3]benzodiazepine, melting point 255–260° C. (ethanol), (starting material from Example 39).
6-(4-Aminophenyl)-8-methoxy-3-n-propyl-11H-imidazo[1,2-c][2,3]benzodiazepine, melting point 183–185° C., (starting material from Example 41).

EXAMPLE 29

9-Methyl-5-(4-nitrophenyl)-11H-1,3-dioxolo[4.5-h]imidazo[1,2-c][2,3]benzodiazepine

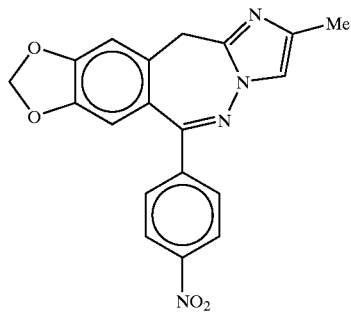

1.70 g (4.99 mmol) of 5-(4-nitrophenyl)-8,9-dihydro-7H-1,3-dioxolo[4,5-h][2,3]-benzodiazepine-8-thione (Example 15D) and 1.17 g (10.0 mmol) of 2-(1-aminoethyl)-1,3-dioxolane (Shinzo Kano i.a.: Heterocycles 26, 1987, 2805) are stirred with 1.08 g of red mercury oxide in Methyl Cellosolve® (50 ml) and heated for 36 hours to 120° C. The mixture is then filtered and concentrated by evaporation to a volume of 5 ml. The intermediate product that precipitates during cooling is suctioned off and dissolved in a 1:1 mixture of concentrated hydrochloric acid and ethanol (25 ml) and heated to boiling for 1.5 hours. After cooling, the hydrochloride of the title compound is isolated.

Yield: 0.70 g (35%), melting point 252–254° C.

EXAMPLE 30

5-(4-Aminophenyl)-9-methyl-11H-1,3-dioxolo[4,5-h]imidazo[1,2-c][2.3]benzodiazepine

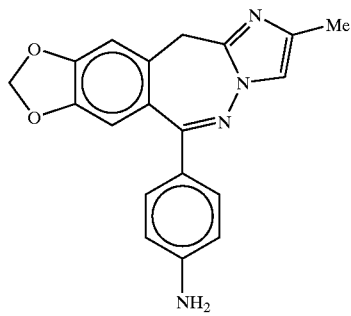

The reduction of the compound of Example 29 is performed according to Example 2.

Yield: 0.37 g (62%), melting point 165–166° C. (ethanol).

EXAMPLE 31

8-Cyclopropyl-5-(4-nitrophenyl)-11H-1,3-dioxolo[4,5-h]imidazo[1,2-c][2,3]benzodiazepine

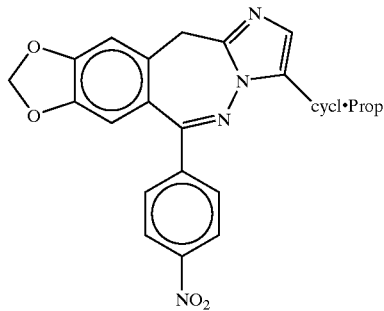

A suspension of 0.50 g (1.47 mmol) of 5-(4-nitrophenyl)-8,9-dihydro-7H-1,3-dioxolo[4,5-h][2,3]benzodiazepine-8-thione (Example 15D) and 0.42 g (2.94 mmol) of 2-aminomethyl-2-cyclopropyl-1,3-dioxolane in 12 ml of Methyl Cellosolve® with 0.32 g (1.47 mmol) of red mercury oxide is stirred for 12 hours at 110° C. After filtration, the mixture is concentrated by evaporation to a volume of 5 ml and poured into water. The precipitate is suctioned off and dissolved in 10 ml of a 1:1 mixture of concentrated hydrochloric acid and glacial acetic acid and heated to boiling for 1.5 hours. During cooling, the hydrochloride salt of the title compound precipitates.

Yield: 0.35 g (56%), melting point 223–225° C.

EXAMPLE 32

5-(4-Aminophenyl)-8-cyclopropyl-11H-1,3-dioxolo[4,5-h]imidazo[1,2-c][2.3]benzodiazepine

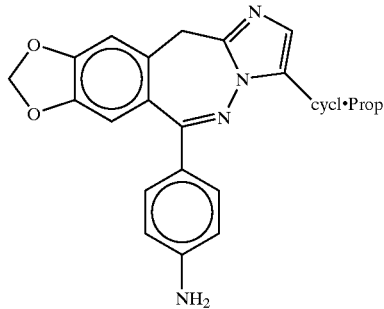

The nitro compound that is produced according to Example 31 is reduced analogously to Example 2. The crude product is purified by column chromatography (silica gel, eluant chloroform: methanol=95:5).

Yield: 0.25 g (85%), melting point 227–229° C. (ethanol).

EXAMPLE 33

8-Methyl-5-(4-nitrophenyl)-11H-1,3-dioxolo[4,5-h]imidazo[1,2-c][2,3]benzodiazepine

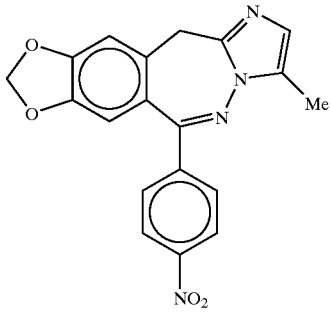

The reaction is performed analogously to Example 31 from 2.0 g (5.86 mmol) of the thione compound of Example 15D and 1.37 g (11.71 mmol) of 2-aminomethyl-2-methyl-1,3-dioxolane (Jiro Adachi and Nobuhiro Sato: J. Org. Chem. 37, 1972, 221) with 1.27 g (5.86 mmol) of red mercury oxide. The rings of the isolated intermediate compound are closed by boiling in 50 ml of glacial acetic acid for 5 hours. Then, it is evaporated to the dry state, and the residue is dissolved in 10% sodium carbonate solution and ethyl acetate. After the organic phase is concentrated by evaporation, the crude product is purified by column chromatography (silica gel, eluant chloroform:methanol=95:5).

Yield: 0.80 g (38%), melting point 220–222° C.

EXAMPLE 34

5-(4-Aminophenyl)8-methyl-11H-1,3-dioxolo[4,5-h]imidazo[1,2-c][2,3]benzodiazepine

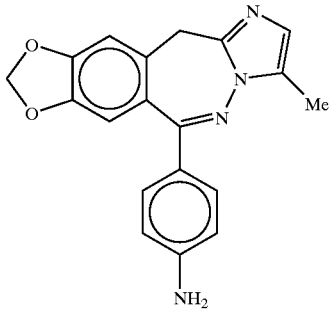

The nitro compound that is produced according to Example 34 is reduced analogously to Example 2.

Yield: 0.51 g (68%), melting point 283–285° C. (ethanol).

EXAMPLE 35

8-Methyl-5-(4-nitrophenyl)-11H-1,3-dioxolo[4,5-h]imidazo[3,4-c][2,3]benzodiazepine

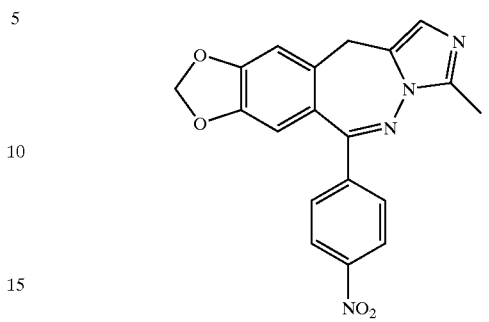

A.
5-(4-Nitrophenyl)-8-(phthalimidomethyl)-9H-1,3-dioxolo[4,5-h][2,3]-benzodiazepine A solution of 1.25 ml (8.05 mmol) of diethyl azodicarboxylate in 7 ml of THF is added in drops to a stirred solution of 2.60 g (7.66 mmol) of 8-hydroxymethyl-5-(4-nitrophenyl)-9H-1,3-dioxolo[4,5-h][2,3]-benzodiazepine (starting compound III.), 2.11 g (8.05 mmol) of triphenylphosphine and 1.18 g (8.05 mmol) of phthalimide in 130 ml of dry THF at room temperature. The mixture is stirred for 24 hours at this temperature. Then, the precipitated product is suctioned off and washed with ethanol. 2.87 g (80%) of the title compound, which can be further processed without further purification, is obtained.

B.
8-Aminomethyl-5-(4-nitrophenyl)-9H-1,3-dioxolo[4,5-h][2,3]-benzodiazepine 0.60 ml (11.7 mmol) of 98% hydrazine hydrate is added to a suspension of 1.10 g (2.35 mmol) of the phthalimido compound from reaction step A in 75 ml of methanol, and the mixture is heated to boiling for 3 hours. After concentration by evaporation, the residue is pulverized with 30 ml of methylene chloride and filtered off. The filtrate is concentrated by evaporation in a vacuum, and the residue is brought to crystallization with water. After suctioning-off, 0.72 g (90%) of the product with a melting point of 143–146° C., which is suitable for the next step without further purification, is obtained.

C.
8-Acetaminomethyl-5-(4-nitrophenyl)-9H-1,3-dioxolo[4,5-h][2,3]-benzodiazepine 0.72 g (2.13 mmol) of the aminomethyl compound from step B is dissolved in 6 ml of acetic anhydride at 25° C. and allowed to stand for 1 hour. The solution is diluted with ice water (30 ml) and stirred for 2 hours. The precipitated substance is filtered and, after drying by column chromatography, purified (silica gel, eluant ethyl acetate:benzene=4:1). After the fractions are concentrated by evaporation, 0.65 g of crystalline substance is obtained, which after washing with ethanol yields 0.56 g (70%) of pure title compound with a melting point of 205° C. (decomposition).

D.
8-Methyl-5-(4-nitrophenyl)-11H-1,3-dioxolo[4,5-h]imidazo[3,4-c][2,3]benzodiazepine 0.40 g (1.05 mmol) of the acetamido compound of step C is suspended in 20 ml of methylene chloride and mixed with 0.48 ml (5.3 mmol) of phosphorus oxychloride. Then, the mixture is heated to boiling for 3 hours. After concentration by evaporation, the residue is taken up in methylene chloride (30 ml) and washed with sodium bicarbonate solution and water, dried, filtered and concentrated by evaporation. 0.38 g of solid substance, which is purified by column chromatography, is obtained (silica gel, eluant chloroform:methanol=95:5). 0.32 g (84%) of pure title compound with a melting point of 305–310° C. (decomposition) is obtained.

Produced analogously via corresponding stages C–D, whereby the method used for acylation is placed in parentheses, are 5-(4-Nitrophenyl)-11H-1,3-dioxolo[4,5-h]imidazo[3,4-c][2,3]benzodiazepine (formic acid, DCC)
5-phenyl-11H-1,3-dioxolo[4,5-h]imidazo[3,4-c][2,3]benzodiazepine (formic acid, DCC)
8-cyclopropyl-5-(4-nitrophenyl)-11H-1,3-dioxolo[4,5-h]imidazo[3,4-c][2,3]benzodiazepine (acid chloride)
5-(4-nitrophenyl)-8-n-propyl-11H-1,3-dioxolo[4,5-h]imidazo[3,4-c][2,3]benzodiazepine (acid chloride)

EXAMPLE 36

5-(4-Aminophenyl)-8-methyl-11H-1,3-dioxolo[4,5-h]imidazo[3,4-c][2,3]benzodiazepine

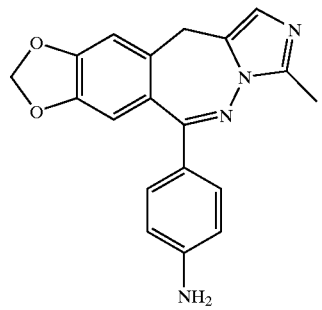

The nitro compound (0.30 g, 0.83 mmol) that is produced according to Example 35 is reduced analogously to Example 2. 0.22 g (81%) of the title compound with a melting point of 282–284° C. (decomposition) is obtained.

Produced analogously are:

5-(4-Aminophenyl)-11H-1,3-dioxolo[4,5-h]imidazo[3,4-c][2,3]benzodiazepine
8-cyclopropyl-5-(4-aminophenyl)-11H-1,3-dioxolo[4,5-h]imidazo[3,4-c][2,3]benzodiazepine
5-(4-aminophenyl)-8-n-propyl-11H-1,3-dioxolo[4,5-h]imidazo[3,4-c][2,3]benzodiazepine

EXAMPLE 37

8-Ethyl-5-(4-nitrophenyl)-11H-1,3-dioxolo[4,5-h]imidazo[3,4-c][2,3]-benzodiazepine

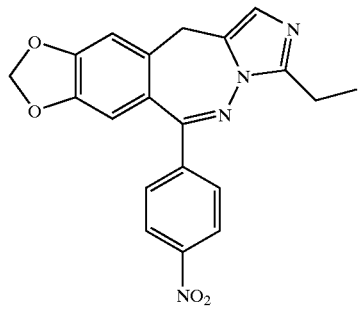

A.
8-Azidomethyl-5-(4-nitrophenyl)-9H-1,3-dioxolo[4,5-h][2,3]-benzodiazepine

A solution of 3.06 g (9.0 mmol) of 8-hydroxymethyl-5-(4-nitrophenyl)-9H-1,3-dioxolo[4,5-h][2,3]-benzodiazepine (starting compound III.) and 2.58 g (9.9 mmol) of triphenylphosphine in 100 ml of dry tetrahydrofuran is mixed with 13.5 ml of a 1.2N hydrazoic acid solution in toluene, then a solution of 1.74 ml (9.9 mmol) of azodicarboxylic acid-diethyl ester is added, and the mixture is stirred for another 2 hours. The precipitated product is suctioned off and washed with tetrahydrofuran and n-hexane. 2.23 g (68%) of the title compound with a melting point of 198–200° C. is obtained.

B.
8-Ethyl-5-(4-nitrophenyl)-11H-1,3-dioxolo[4,5-h]imidazo][3,4-c][2,3]benzodiazepine 1.98 g (5.4 mmol) of the compound from step A is dissolved in 100 ml of dry THF and mixed with 1.56 g (5.94 mmol) of triphenylphosphine and stirred for 4 hours. Then, the solution is cooled to −50° C., and a solution of 0.78 ml (6.0 mmol) of propionic acid anhydride in 3 ml of THF is added. After 1 hour at −50° C., the mixture is stirred overnight at room temperature. The reaction mixture is then diluted with diethyl ether and washed with 10% sodium bicarbonate solution and water, dried and concentrated by evaporation. The residue is purified by column chromatography on silica gel. (Gradient elution: beginning with n-hexane: ethyl acetate=1:1, then with a constantly increasing proportion of ethyl acetate).

1.0 g of a product which, after being boiled up in 5 ml of ethyl acetate, yields 0.75 g of a mixture of substances, which consists of the title compound and the intermediate compound 8-propionylaminomethyl-5-(4-nitrophenyl)-9H-1,3-dioxolo[4,5-h][2,3]-benzodiazepine, is obtained.

To complete the closure of the rings, the above mixture is dissolved in anhydrous dichloroethane and, after 0.20 ml (2.15 mmol) of phosphorus oxychloride is added, heated to boiling for 2 hours. The cooled reaction mixture is then washed with sodium bicarbonate solution and evaporated to the dry state.

0.65 g (33%) of the title compound with a melting point of 243–245° C. is obtained.

EXAMPLE 38

5-(4-Aminophenyl)-8-ethyl-11H-1,3-dioxolo[4,5-h]imidazo[3,4-c][2,3]benzodiazepine

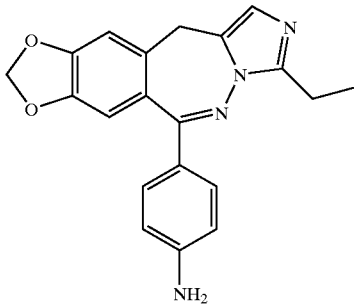

0.38 g (1.0 mmol) of the nitro compound that is produced according to Example 37 is reduced in 10 ml of a 1:1 mixture of methylene chloride and methanol according to Example 2. The crude product is purified by column chromatography (silica gel, eluant: chloroform:methanol=95:5).

0.28 g (81%) of the title compound with a melting point of 135–138° C. is obtained.

EXAMPLE 39

9-Ethyl-5-(4-nitrophenyl)-11H-1,3-dioxolo[4,5-h]imidazo59[1,2-c][2,3]benzodiazepine

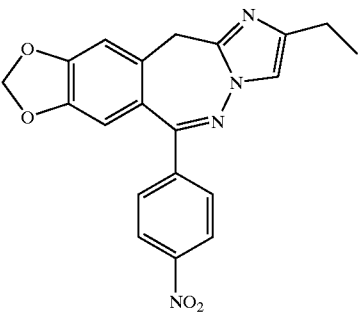

After a catalytic amount of p-toluenesulfonic acid is added, a mixture of 1.0 g (2.82 mmol) of 8-methylthio-5-(4-nitrophenyl)-9H-1,3dioxolo[4,5-h][2,3]-benzodiazepine (Example 15, step E) and 0.74 g (5.64 mmol) of 2-(1-aminopropyl)-1,3-dioxolane (J. Org. Chem. 21, 1956, 115) in 60 ml of Methyl Cellosolve® is stirred for 48 hours at 120° C. After cooling, the unchanged methylthio compound is filtered out, and the filtrate is concentrated by evaporation to a volume of 10 ml. After 50 ml of water is added, the intermediate compound of the condensation step precipitates and is suctioned off. The filter residue is dissolved in 10 ml of ethanol:concentrated hydrochloric acid=1:1 and heated to boiling for 1.5 hours. Then, the solution is concentrated by evaporation, and the residue is taken up in 50 ml of water. It is neutralized with sodium carbonate and extracted with ethyl acetate, dried, filtered and concentrated by evaporation. The residue is purified by column chromatography (silica gel, eluant: chloroform:methanol=95:5). 0.38 g (36%) of the title compound with a melting point of 188–190° C. is obtained.

Produced analogously are:
9-Bromo-8-methoxy-3-methyl-6-(4-nitrophenyl)-11H-imidazo[1,2-c][2,3]benzodiazepine, melting point: 196–200° C.
9-bromo-8-methoxy-2-methyl-6-(4-nitrophenyl)-11H-imidazo[1,2-c][2,3]benzodiazepine, melting point 265–268° C. (ethanol).

(Starting material is in each case the compound of Example 27B).

EXAMPLE 40

5-(4-Aminophenyl)-9-ethyl-11H-1,3-dioxolo[4,5-h]imidazo[1,2-c][2,3]benzodiazepine

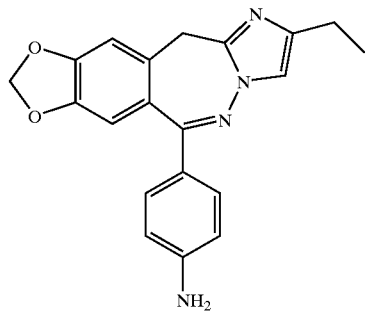

The nitro compound of Example 39 is reduced in methylene chloride:methanol=1:1 analogously to Example 2. After recrystallization from ethyl acetate, 0.14 g (41%) of the title compound with a melting point of 192–194° C. is obtained.

EXAMPLE 41

5-(4-Nitrophenyl)-8-propyl-11H-1,3-dioxolo[4,5-h]imidazo[1,2-c][2.3]benzodiazepine hydrochloride

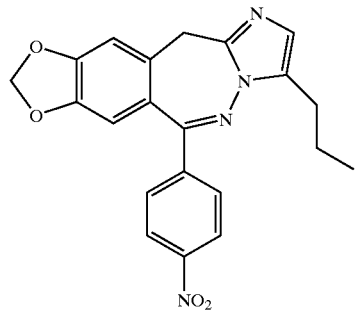

Produced from 0.68 g (2.0 mmol) of the thione compound (Example 15, step D) and 0.58 g (4.0 mmol) of 2-aminomethyl-2-propyl-1,3-dioxolane (produced analogously to J. Org. Chem., 37, 1972, 221) and 0.43 g (2.0 mmol) of red mercury oxide according to Example 29. After 10 hours at 110° C., the intermediate compound of the condensation step is purified by chromatography (silica gel, eluant: chloroform-methanol=95:5). Ring-closure reaction is implemented by heating the intermediate product in a 1:1 mixture of acetic acid and concentrated hydrochloric acid.

After the concentration by evaporation, 0.36 g of the title compound is obtained as hydrochloride salt.

Yield 42%, melting point 200–201° C.

Produced analogously is:

9-Bromo-8-methoxy-6-(4-nitrophenyl)-3-n-propyl-11H-imidazo[1,2-c][2,3]benzodiazepine, melting point 150–162° C.

EXAMPLE 42

5-(4-Aminophenyl)-8-propyl-11H-1,3-dioxolo[4,5-h]imidazo[1,2-c][2,3]benzodiazepine

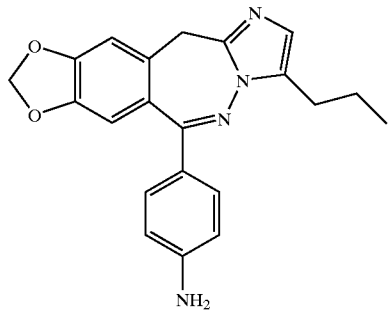

The nitro compound of Example 41 is reduced analogously to Example 2. After recrystallization from ethanol, 0.27 g (89%) of the title compound with a melting point of 175–176° C. (from ethanol) is obtained.

EXAMPLE 43

8-Ethyl-5-(4-nitrophenyl)-11H-1,3-dioxolo[4,5-h]imidazo[1,2-c][2,3]-benzodiazepine hydrochloride

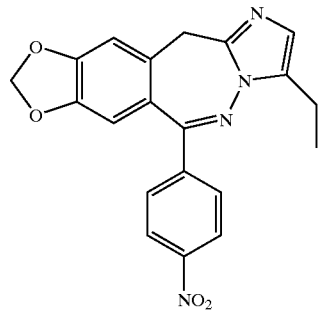

Produced analogously to Example 41 from 0.68 g (2.0 mmol) of the thione compound (Example 15, step D) and 0.53 g (4.0 mmol) of 2-aminomethyl-2-ethyl-1,3-dioxolane (production analogous to J. Org. Chem., 37, 1972, 221). The title compound is isolated as hydrochloride (0.32 g).

Yield: 39%, melting point 217–218° C.

EXAMPLE 44

5-(4-Aminophenyl)-8-ethyl-11H-1,3-dioxolo[4,5-h]imidazo[1,2-c][2,3]benzodiazepine

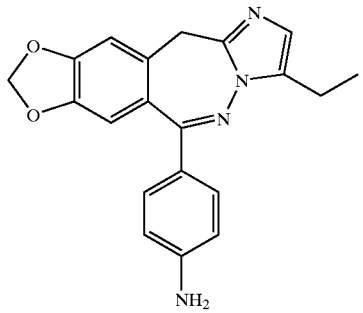

Produced from the nitro compound of Example 43 according to Example 2. 0.18 g of the title compound is obtained. Yield: 67%, melting point 258–260° C. (ethanol).

EXAMPLE 45

8,9-Dimethyl-5-(4-nitrophenyl)-11H-[1,3-dioxolo[4,5-h]imidazo[1,2-c][2,3]benzodiazepine hydrochloride

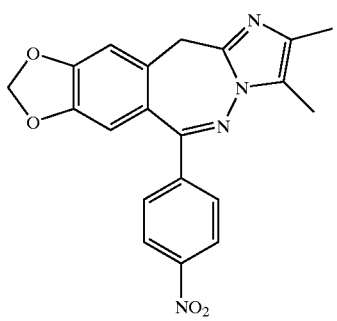

The title compound is produced analogously to Example 29 from 2.0 g (5.86 mmol) of the thioxo compound of Example 15, step D and 1.54 g (11.72 mmol) of 2-(1-aminoethyl)-2-methyl-1,3-dioxolane (J. Org. Chem. 37, 1972, 221) with 1.279 (5.86 mmol) of red mercury oxide. The condensation step takes about 30 hours at 110° C. The intermediate product is purified by chromatography as in Example 41 and then the rings are closed by boiling in 10 ml of a mixture that consists of ethanol-concentrated hydrochloric acid. The title compound is isolated as hydrochloride: 0.52 g (22%), melting point 240–243° C.

Produced analogously is:

9-Bromo-2,3-dimethyl-8-methoxy-6-(4-nitrophenyl)11H-imidazo[1,2-c][2,3]benzodiazepine, melting point: 190–193° C.

EXAMPLE 46

5-(4-Aminophenyl)-8,9-dimethyl-11H-1,3-dioxolo[4,5-h]imidazo[1,2-c][2,3]benzodiazepine

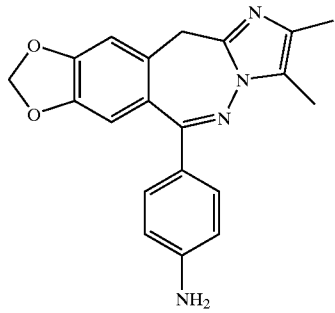

The nitro compound of Example 45 is reduced according to Example 2. 0.33 g (75%) of the title compound with a melting point of 226–227° C. (ethanol) is obtained.

EXAMPLE 47

A.
4-Nitrobenzoylhydrazone of 2-hydroxy-4-methoxybenzaldehyde 63.4 g of 4-nitrobenzhydrazide is introduced into 2.5 l of 1-propanol and mixed with 53.3 g of 2-hydroxy-4-methoxybenzaldehyde and refluxed for 1 hour. After cooling in an ice bath, it is suctioned off. 104 g of the 4-nitrobenzoylhydrazone of 2-hydroxy-4-methoxybenzaldehyde is obtained.

Produced analogously are:
Benzoylhydrazone of 2-hydroxy-4-methoxybenzaldehyde
4-bromobenzoylhydrazone of 2-hydroxy-4-methoxybenzaldehyde B.
2-(4-Nitrobenzoyl)-4-methoxybenzaldehyde 50 g of 4-nitrobenzoylhydrazone of 2-hydroxy-4-methoxybenzaldehyde is introduced into 1.5 l of tetrahydrofuran (dried on a molecular sieve) at 8° C. and mixed in portions with 99.4 g of lead(IV) acetate (85%). After addition is completed, it is stirred for 30 more minutes, suctioned off, and the filtrate is concentrated by evaporation. The residue is taken up in ethyl acetate, washed in succession with water and common salt solution, dried, filtered and concentrated by evaporation. After recrystallization from ethyl acetate, 22.8 g of 2-(4-nitrobenzoyl)-4-methoxybenzaldehyde is obtained.

Produced analogously are:
2-Benzoyl-4-methoxybenzaldehyde
2-(4-bromobenzoyl)-4-methoxybenzaldehyde C.
1-Methoxy-2-(4-methoxy-2-(4-nitrobenzoyl)phenyl)ethylene 10 g of 2-(4-nitrobenzoyl)-4-methoxybenzaldehyde is introduced together with 18 g of (methoxymethyl)triphenylphosphonium chloride in 400 ml of toluene and mixed in portions with 5.9 g of potassium-tert-butylate while being cooled with ice. After 1 hour of stirring while being cooled with ice and a subsequent 3.5 hours of stirring at room temperature, it is mixed with 200 ml of water, weakly acidified with 1N hydrochloric acid and extracted three times with ethyl acetate. The ethyl acetate phases are washed with saturated common salt solution, dried, filtered and concentrated by evaporation. The residue is chromatographed on silica gel with hexane:ethyl acetate=1:1 as an eluant. 6.9 g of 1-methoxy-2-(4-methoxy-2-(4-nitrobenzoyl)phenyl)ethylene as a mixture of the E- and Z-forms is obtained.

Produced analogously are:
1-Methoxy-2-(4-methoxy-2-benzoylphenyl)ethylene.
1-Methoxy-2-(4-methoxy-2-(4-bromobenzoyl)phenyl)ethylene.

D.
2-(4-Methoxy-2-(4-nitrobenzoyl)phenyl)acetic acid 6.9 g of 1-methoxy-2-(4-methoxy-2-(4-nitrobenzoyl)ethylene as a mixture of the E- and Z-forms is introduced into 310 ml of tetrahydrofuran and mixed with 100 ml of 1N hydrochloric acid. After stirring overnight at room temperature, it is diluted with 300 ml of water, and the tetrahydrofuran is distilled off at a bath temperature of 30° C. The aqueous phase is extracted three times with ethyl acetate. The collected organic phase is washed with water, dried, filtered and concentrated by evaporation. It is taken up in 300 ml of acetone and mixed drop by drop with 11.8 ml of 8N Jones reagent at 4° C. After the addition is completed, it is stirred for 2 more hours at this temperature, mixed with 6 ml of isopropanol and stirred for another 15 minutes. It is then diluted with 200 ml of water, and the acetone is drawn off in a rotary evaporator. The aqueous phase is extracted three times with ethyl acetate, and the collected organic phase is washed with water, dried, filtered and concentrated by evaporation. After recrystallization from ethyl acetate/hexane, 6.3 g of 2-(4-methoxy-2-(4-nitrobenzoyl)phenyl)acetic acid is obtained.

Produced analogously are:
2-(4-Methoxy-2-benzoylphenyl) acetic acid
2-(4-methoxy-2-(4-bromobenzoyl)phenyl) acetic acid E.
8-Methoxy-1-(4-nitrophenyl)-4,5-dihydro-3H-2,3-benzodiazepin-4-one 7.8 g of 2-(4-methoxy-2-(4-nitrobenzoyl)phenyl)acetic acid is mixed in 200 ml of tetrahydrofuran with 2.3 ml of 80% hydrazine hydrate and stirred for 6 hours at room temperature. After standing overnight, it is mixed with 50 ml of water, and the tetrahydrofuran is drawn off in a rotary evaporator. The precipitated 2-(4-methoxy-2-(4-nitrobenzoyl)phenyl)acetic acid hydrazide (4.9 g) is suctioned off and stirred in 37 ml of glacial acetic acid at room temperature for 2 hours. It is diluted with 37 ml of water and suctioned off. 4.37 g of 8-methoxy-1-(4-nitrophenyl)-4,5-dihydro-3H-2,3-benzodiazepin-4-one with a melting point of 282° C. is obtained.

Produced in a basically similar way but with the mixed acid anhydride with isobutyl chloroformate are:
8-Methoxy-1-phenyl-4,5-dihydro-3H-2,3-benzodiazepin-4-one
8-methoxy-1-(4-bromophenyl)-4,5-dihydro-3H-2,3-benzodiazepin-4-one F.
8-Methoxy-1-(4-nitrophenyl)-4,5-dihydro-3H-2,3-benzodiazepine-4-thione 4.3 g of 8-methoxy-1-(4-nitrophenyl)-4,5-dihydro-3H-2,3-benzodiazepin-4-one is mixed in 48 ml of pyridine with 2.46 g of diphosphorus pentasulfide and stirred under argon and with exclusion of moisture for 2 hours at a bath temperature of 100° C. It is diluted with water, and the precipitated product is suctioned off. After chromatography on silica gel first with ethyl acetate:hexane=1:1 and later with ethyl acetate, a total of 3.13 g of 8-methoxy-1-(4-nitrophenyl)-4,5-dihydro-3H-2,3-benzodiazepine-4-thione is obtained.

Produced analogously are:
8-Methoxy-1-phenyl-4,5-dihydro-3H-2,3-benzodiazepine-4-thione
8-methoxy-1-(4-bromophenyl)-4,5-dihydro-3H-2,3-benzodiazepine-4-thione G.
8-Methoxy-3-methyl-6-phenyl-11H-imidazo[1,2-c][2,3]benzodiazepine

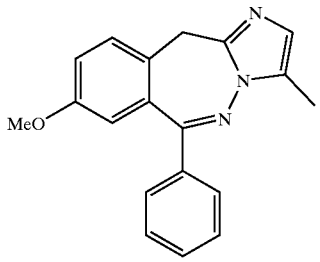

500 mg of 8-methoxy-1-phenyl-4,5-dihydro-3H-2,3-benzodiazepine-4-thione is stirred in 1.5 ml of ethylene glycol monomethyl ether (Cellosolve® and 548 mg of 2-aminomethyl-2-methyl-1,3-dioxolane while argon is passing through it for 10 hours at 60° C. After filtration and washing with cold ethanol and diisopropyl ether, 550 mg of imino compound, which is dissolved in 10 ml of ethanol, mixed with 10 ml of concentrated hydrocholoric acid and refluxed for 3 hours, is obtained. It is added to water, set at pH 11 and extracted with ethyl acetate. The ethyl acetate phase is washed with water, dried, filtered and concentrated by evaporation. After recrystallization from ethyl acetate/diisopropyl ether, 240 mg of 8-methoxy-3-methy-6-phenyl-11H-imidazo[1,2-c][2,3]benzodiazepine with a melting point of 140° C. is obtained.

Produced analogously from the corresponding thiones are:
8-Methoxy-2-methyl-6-phenyl-11H-imidazo[1,2-c][2,3]benzodiazepine
8-methoxy-3-methyl-6-phenyl-11H-imidazo[1,2-c][2,3]benzodiazepine
8-methoxy-3-ethyl-2-methyl-6-phenyl-11H-imidazo[1,2-c][2,3]benzodiazepine
8-methoxy-6-phenyl-3-(4-pyridyl)-11H-imidazo[1,2-c][2,3]benzodiazepine[2]
8-methoxy-6-phenyl-3-(2-pyridyl)-11H-imidazo[1,2-c][2,3]benzodiazepine[2]
8-methoxy-6-phenyl-3-(3-pyridyl)-11H-imidazo[1,2-c][2,3]benzodiazepine[2]
3,6-diphenyl-8-methoxy-2-methyl-11H-imidazo[1,2-c][2,3]benzodiazepine
8-methoxy-6-(4-nitrophenyl)-3-(2-pyridyl)-11H-imidazo[1,2-c][2,3]benzodiazepine
8-methoxy-6-(4-nitrophenyl)-3-(4-pyridyl)-11H-imidazo[1,2-c][2,3]benzodiazepine
5-(4-chlorophenyl)-8,9-dimethyl-11H-1,3-dioxolo[4,5-h]imidazo[1,2-c][2,3]benzodiazepine
9-ethyl-8-methyl-5-(4-nitrophenyl)-11H-1,3-dioxolo[4,5-h]imidazo[1,2-c][2,3]benzodiazepine
8-ethyl-9-methyl-5-(4-nitrophenyl)-11H-1,3-dioxolo[4,5-h]imidazo[1,2-c][2,3]benzodiazepine
5-(4-nitrophenyl)-8-(4-pyridyl)-11H-1,3-dioxolo[4,5-h]imidazo[1,2-c][2,3]benzodiazepine[2]
8,9-dimethyl-5-phenyl-11H-1,3-dioxolo[4,5-h]imidazo[1,2-c][2,3]benzodiazepine

[2]The corresponding ketals are produced according to Org. Synth. 64, 19, (1986).

EXAMPLE 48

2,3-Dimethyl-6-(4-nitrophenyl)-8-methoxy-11H-imidazo[1,2-c][2.3]benzodiazepine

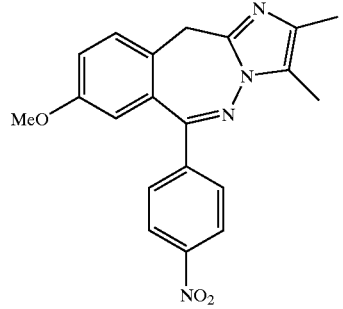

2.3 g of 8-methoxy-1-(4-nitrophenyl)-4,5-dihydro-3H-2,3-benzodiazepine-4-thione is stirred with 3 ml of 2-amino-3,3-dimethoxybutane (produced by reductive amination according to J. Org. Chem. 52, (12), 2616 from 3,3-dimethoxybutan-2-one) while argon is passing through it for 4 hours at a bath temperature of 110° C. The preparation is mixed with 50 ml of 1N hydrochloric acid, diluted with water to 100 ml and extracted three times with 150 ml of ethyl acetate each. The aqueous phase is made alkaline with a 1N sodium hydroxide solution and extracted three times with ethyl acetate. The collected organic phases are dried, filtered and concentrated by evaporation, and the residue is chromatographed on silica gel with methylene chloride:ethanol=10:1 as an eluant. 1.5 g of 2,3-dimethyl-8-methoxy-6-(4-nitrophenyl)-11H-imidazo[1,2-c]benzodiazepine is obtained.

Produced analogously are:
6-(4-Bromophenyl)-2,3-dimethyl-8-methoxy-11H-imidazo[1,2-c][2,3]benzodiazepine
2,3-dimethyl-8-methoxy-6-phenyl-11H-imidazo[1,2-c][2,3]benzodiazepine
8,9-dimethyl-5-(4-fluorophenyl)-11H-1,3-dioxolo[4,5-h]imidazo[1,2-c][2,3]benzodiazepine

EXAMPLE 49

A. 6-(4-Aminophenyl)-2,3-dimethyl-8-methoxy-11H-imidazo[1,2-c][2,3]benzodiazepine

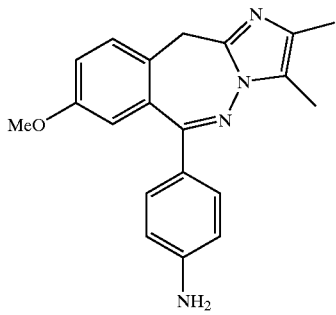

834 mg of 2,3-dimethyl-8-methoxy-6-(4-nitrophenyl)-11H-imidazo[1,2-c][2,3]benzodiazepine in 33 ml of glacial acetic acid together with 2.25 g of iron powder are heated for 20 minutes in an oil bath that is preheated to 90° C. It is suctioned off hot and rewashed with glacial acetic acid. The filtrate is concentrated by evaporation, and the residue is dispersed in ethyl acetate and 1N sodium hydroxide solution. The aqueous phase is shaken out twice with ethyl acetate, and the collected organic phase is washed with water, dried, filtered and concentrated by evaporation. This residue is chromatographed on silica gel with methylene chloride:ethanol=10:1 as an eluant. After the corresponding fractions that are concentrated by evaporation are absorptively precipitated with ethyl acetate/hexane, 331 mg of 6-(4-aminophenyl)-2,3-dimethyl-8-methoxy-11H-imidazo[1,2-c][2,3]benzodiazepine with a melting point of 280° C. is obtained.

Produced analogously are:
6-(4-Aminophenyl)-8-methoxy-3-(2-pyridyl)-11H-imidazo[1,2-c][2,3]benzodiazepine
6-(4-aminophenyl)-8-methoxy-3-(4-pyridyl)-11H-imidazo[1,2-c][2,3]benzodiazepine
5-(4-aminophenyl)-9-bromo-8-methyl-11H-1,3-dioxolo[4,5-h]imidazo][1,2-c][2,3]benzodiazepine
5-(4-aminophenyl)-8-bromo-9-methyl-11H-1,3-dioxolo[4,5-h]imidazo[1,2-c][2,3]benzodiazepine B. 5-(4-Aminophenyl)-8-ethyl-9-methyl-11H-1,3-dioxolo[4,5-h]imidazo[1,2c-][2,3]benzodiazepine

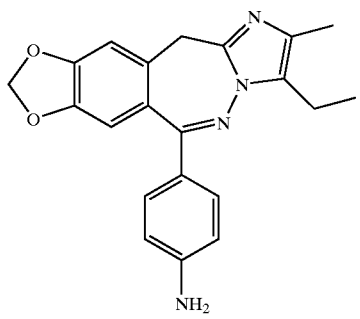

527 mg of 8-ethyl-9-methyl-5-(4-nitrophenyl)-11H-1,3-dioxolo[4,5-h]imidazo[1,2-c][2,3]benzodiazepine is mixed in 11 ml of ethanol with 5.4 ml of cyclohexene and 106 mg of palladium hydroxide on carbon (Pearlman's catalyst), and it is stirred for 3 hours at a bath temperature of 110° C. After catalyst is filtered out, it is concentrated by evaporation, and the residue is chromatographed on silica gel with ethyl acetate as an eluant. After combining the corresponding fractions and recrystallization from ethanol, 348 mg of 5-(4-aminophenyl)-8-ethyl-9-methyl-11H-1,3-dioxolo[4,5-h]imidazo[1,2-c][2,3]benzodiazepine with a melting point of 227–228° C. is obtained.

Produced analogously are:
5-(4-Aminophenyl)-8-(4-pyridyl)-11H-1,3-dioxolo[4,5-h]imidazo[1,2-c][2,3]benzodiazepine
5-(4-aminophenyl)-9-ethyl-8-methyl-11H-1,3-dioxolo[4,5-h]imidazo[1,2-c][2,3]benzodiazepine

EXAMPLE 50

8-Methyl-5-phenyl-11H-1,3-dioxolo[4,5-h]imidazo[1,2-c][2,3]benzodiazepine

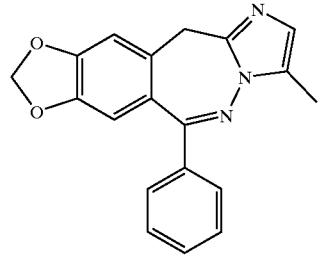

200 mg of 5-(4-aminophenyl)-8-methyl-11H-1,3-dioxolo[4,5-h]imidazo[1,2-c][2,3]benzodiazepine is mixed in 30 ml of tetrahydrofuran with 1.32 ml of pentyl nitrite and refluxed under argon for 2 hours. After concentration by evaporation, it is chromatographed on silica gel with methylene chloride:ethanol=10:1. 136 mg of 8-methyl-5-phenyl-11H-1,3-dioxolo[4,5-h]imidazo[1,2-c][2,3]benzodiazepine is obtained.

EXAMPLE 51

5-(4-Chlorophenyl)-8-methyl-11H-1,3-dioxolo[4,5-h]imidazo[1,2-c][2,3]benzodiazepine

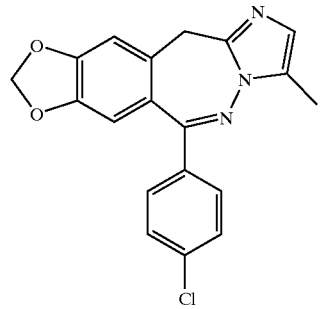

160 mg of 5-(4-aminophenyl)-8-methyl-11H-1,3-dioxolo[4,5-h]imidazo[1,2-c][2,3]benzodiazepine is dissolved in 2 ml of water and 2 ml of concentrated hydrochloric acid, and it is diazotized at 0° C. with a solution of 36 mg of sodium nitrite in 0.5 ml of water. Stirring is continued for 45 minutes at 0° C. To this solution at room temperature is added in drops a solution which is prepared as follows: 256 mg of copper sulfate pentahydrate is mixed in 1 ml of water with 87 mg of sodium chloride and mixed drop by drop with a solution of 68 mg of sodium sulfite in 0.6 ml of water. The white precipitate is separated from the supernatant by decanting, washed twice with water and dissolved in concentrated hydrochloric acid. After this solution is added, it is heated for 10 minutes in a steam bath and stirred for 1 more hour at room temperature. It is diluted with water, made alkaline with ammonia solution and extracted with ethyl acetate. The ethyl acetate phase is washed with saturated sodium chloride solution, dried, filtered and concentrated by evaporation. After chromatography on silica gel with methylene chloride:ethanol=10:1, 87 mg of 5-(4-chlorophenyl)-8-methyl-11H-1,3-dioxolo[4,5-h]imidazo[1,2-c][2,3]benzodiazepine is obtained.

EXAMPLE 52

5-(4-Fluorophenyl)-8-methyl-11H-1,3-dioxolo[4,5-h]imidazo[1,2-c][2,3]benzodiazepine

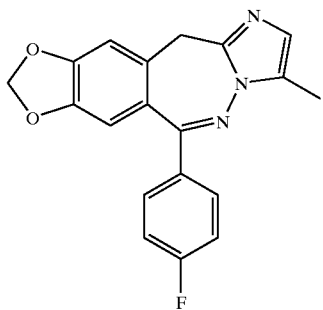

First 200 mg of 5-(4-aminophenyl)-8-methyl-11H-1,3-dioxolo[4,5-h]imidazo[1,2-c][2,3]benzodiazepine is added to a solution of 6 ml of hydrogen fluoride-pyridine complex (1:1) under argon, and then 51 mg of sodium nitrite is added at 0–5° C. After stirring at 5–10° C. for 40 minutes, 117 mg of tin(II) chloride and 190 mg of tetrabutylammonium dihydrogen trifluoride are added to the preparation. It is then heated for 3 hours to a bath temperature of 100° C. After cooling, it is added to ice water and extracted three times with ethyl acetate and three times with methylene chloride. The collected organic phase is dried, filtered, concentrated by evaporation and chromatographed on silica gel first with methylene chloride:ethanol=10:1, then a second time with acetone:ethyl acetate=3:1 and then a third time with methylene chloride:ethanol=95:5. 106 mg of 5-(4-fluorophenyl)-8-methyl-11H-1,3-dioxolo[4,5-h]imidazo[1,2-c][2,3]benzodiazepine with a melting point of 190° C. is obtained.

EXAMPLE 53

9-Bromo-8-methyl-5-(4-nitrophenyl)-11H-1,3-dioxolo[4,5-h]imidazo[1,2-c][2,3]benzodiazepine

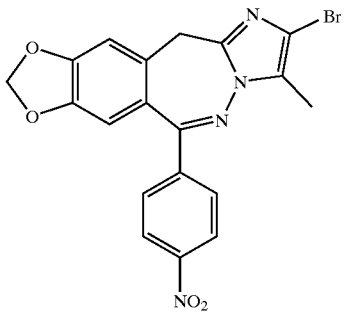

900 mg of 8-methyl-5-(4-nitrophenyl)-11H-1,3-dioxolo[4,5-h]imidazo[1,2-c][2,3]benzodiazepine is mixed in 10 ml of dimethylformamide with 441 mg of N-bromosuccinimide and stirred for 1.5 hours at room temperature. After dilution with 40 ml of water, the precipitated product is suctioned off, and 900 mg of 9-bromo-8-methyl-5-(4-nitrophenyl)-11H-1,3-dioxolo[4,5-h]imidazo[1,2-c][2,3]benzodiazepine is obtained.

Produced analogously are:
8-Bromo-9-methyl-5-(4-nitrophenyl)-11H-1,3-dioxolo[4,5-h]imidazo[1,2-c][2,3]benzodiazepine
2-bromo-8-methoxy-3-methyl-6-phenyl-11H-imidazo[1,2-c][2,3]benzodiazepine
2-bromo-8-methoxy-6-phenyl-3-(3-pyridyl)-11H-imidazo[1,2-c][2,3]benzodiazepine
8,9-dibromo-5-(4-nitrophenyl)-11H-1,3-dioxolo[4,5-h]imidazo[1,2-c][2,3]benzodiazepine (with excess N-bromosuccinimide)
3-bromo-8-methoxy-2-methyl-6-phenyl-11H-imidazo[1,2-c][2,3]benzodiazepine
8-iodo-5-(4-nitrophenyl)-11H-1,3-dioxolo[4,5-h]imidazo[1,2-c][2,3]benzodiazepine with N-iodosuccinimide

EXAMPLE 54

2-Acetyl-3-(3-pyridyl)-8-methoxy-6-phenyl-11H-imidazo[1,2-c][2,3]benzodiazepine

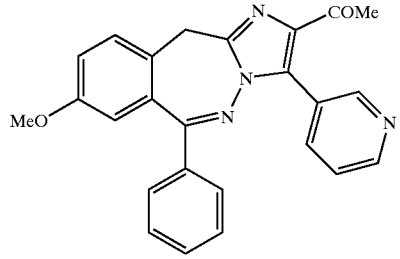

82 mg of 2-bromo-3-(3-pyridyl)-8-methoxy-6-phenyl-11H-imidazo[1,2-c][2,3]benzodiazepine is mixed in 3 ml of toluene and 0.5 ml of dimethylformamide with 650 mg of (1-ethoxyvinyl)tributylstannane and 10 mg of palladium(O) tetrakistriphenylphosphine, and it is heated for 4 hours to a bath temperature of 120° C. Then, (1-ethoxyvinyl)tributylstannane and 10 mg of palladium(O)

tetrakistriphenylphosphine are added again, and it is heated for 10 hours to a bath temperature of 120° C. After cooling, it is mixed with 2 ml of 1N hydrochloric acid, stirred for 10 minutes, made alkaline with ammonia and shaken out with ethyl acetate. The ethyl acetate phase is washed with water and saturated common salt solution, dried, filtered and concentrated by evaporation. After chromatography of the residue on silica gel with ethyl acetate as an eluant, 20 mg of 2-acetyl-3-(3-pyridyl)-8-methoxy-6-phenyl-11H-imidazo[1,2-c][2,3]benzodiazepine is obtained.

Obtained analogously are:
2-Vinyl-3-(3-pyridyl)-8-methoxy-6-phenyl-11H-imidazo[1,2-c][2,3]benzodiazepine,
9-propinyl-5-phenyl-11H-1,3-dioxolo[4,5-h]imidazo[1,2-c][2,3]benzodiazepine with the addition of a Cu(I) co-catalyst.

EXAMPLE 55

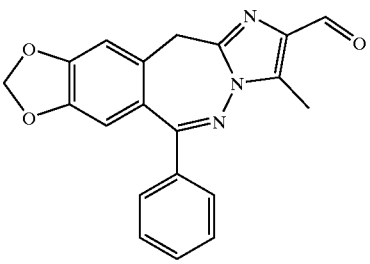

120 mg of 9-bromo-8-methyl-5-phenyl-11H-1,3-dioxolo[4,5-h]imidazo[1,2-c][2,3]benzodiazepine is mixed in 15 ml of tetrahydrofuran at −78° C. with 0.36 ml of butyllithium (hexane, 1 mol) and stirred for 15 minutes. It is then mixed at this temperature with 0.6 ml of dimethylformamide and stirred for 15 minutes. After stirring to room temperature, it is mixed with water, the tetrahydrofuran is distilled off and extracted with ethyl acetate. After the solvent is distilled off, it is chromatographed on silica gel with dichloromethane:ethanol=95:5 as an eluant. 46 mg of 9-formyl-8-methyl-5-phenyl-11H-1,3-dioxolo[4,5-h]imidazo[1,2-c][2,3]benzodiazepine is obtained.

Produced in a basically similar way are:
9-(1-Hydroxyprop-1-yl)-8-methyl-5-phenyl-11H-1,3-dioxolo[4,5-h]imidazo[1,2-c][2,3]benzodiazepine
9-ethyl-8-methyl-5-phenyl-11H-1,3-dioxolo[4,5-h]imidazo[1,2-c][2,3]benzodiazepine
9-methoxymethyl-8-methyl-5-phenyl-11H-1,3-dioxolo[4,5-h]imidazo[1,2-c][2,3]benzodiazepine

EXAMPLE 56

100 mg of 9-iodo-8-methyl-5-phenyl-11H-1,3-dioxolo[4,5-h]-imidazo[1,2-c][2,3]benzodiazepine is provided, dissolved in 4 ml of toluene and 1.5 ml of ethanol. 54 mg of diethyl-3-pyridyl-borane, 20 mg of tetrakis (triphenylphosphine)-palladium (O) and 0.8 ml of a 2 M Na$_2$CO$_3$ solution are added, and it is stirred for 3 hours at 110° C. After water is added, it is extracted using ethyl acetate, and the organic phase is concentrated by evaporation. This residue is chromatographed on silica gel with dichloromethane:ethanol=95:5 as an eluant. 13 mg of 8-methyl-5-phenyl-9-(3-pyridyl)-11H-1,3-dioxolo[4,5-h]imidazo[1,2-c]benzodiazepine is obtained.

Produced analogously from 9-iodo-5-phenyl-11H-1,3-dioxolo[4,5-h]imidazo[1,2-c][2,3]benzodiazepine is:

9-(3-Pyridyl)-5-phenyl-11H-1,3-dioxolo[4,5-h]imidazo[1,2-c][2,3]benzodiazepine

EXAMPLE 57

100 mg of 9-iodo-8-methyl-5-phenyl-11H-1,3-dioxolo[4,5-h]imidazo[1,2-c][2,3]benzodiazepine is stirred in 2 ml of dimethylformamide, 0.03 ml of triethylamine, 0.032 ml (30 mg) of diethyl phosphite and 15 mg of tetrakis (triphenylphosphine)-palladium(O) at 1000° C. for 2 hours. Then, it is diluted with 10 ml of water and extracted with ethyl acetate. The organic phase that is concentrated by evaporation is chromatographed on silica gel with dichloromethane:ethanol=95:5 as an eluant. 10 mg of 8-methyl-5-phenyl-11H-1,3-dioxolo[4,5-h]imidazo[1,2-c][2,3]benzodiazepine-9-phosphonic acid diethyl ester is obtained.

What is claimed is:
1. A compound of Formula V

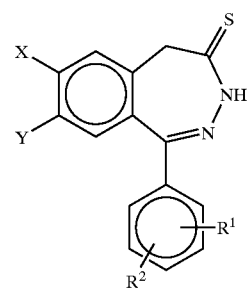

in which
R$^1$ and R$^2$ are the same or different and mean hydrogen, C$_1$–C$_6$ alkyl, nitro, halogen, cyano, —NR$^8$R$^9$, —O—C$_{1-4}$ alkyl, —CF$_3$, OH or C$_{1-6}$ alkanoyloxy,
R$^8$ and R$^9$ are the same or different and mean hydrogen, C$_{1-6}$ alkyl or —CO—C$_{1-6}$ alkyl,
X means hydrogen or halogen,
Y means C$_{1-6}$ alkoxy or X and Y together mean —O—(CH$_2$)$_n$—O—, and
n means 1, 2 or 3,
or a physiologically acceptable salt thereof.
2. A compound of claim 1, in the form of an isomer.
3. A compound of claim 1, wherein X and Y together mean —O—(CH$_2$)—O—, R$^1$ means hydrogen, and R$^2$ means nitro, at the 4-position of the phenol ring.
4. A compound of claim 1, wherein X and Y together mean —O—(CH$_2$)—O—, and R$^1$ and R$^2$ are hydrogen.

5. A compound of Formula VII

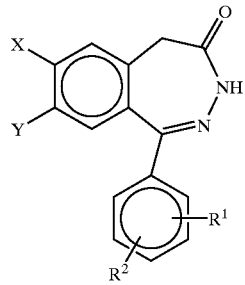

VII in which

R$^1$ hydrogen

R$^2$ is nitro, at the 4-position of the phenol ring,

X and Y together are —O—(CH$_2$)$_n$—O—, and n is 1, 2 or 3, or a physiologically acceptable salt thereof.

6. A compound of Formula VII

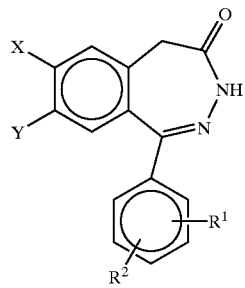

VII in which

R$^1$ and R$^2$ are hydrogen,

X and Y together are —O—(CH$_2$)$_n$—O—, and n is 1, 2 or 3, or a physiologically acceptable salt thereof.

7. A compound of formula IIa or IIIa, or an isomer or physiologically acceptable salt thereof,

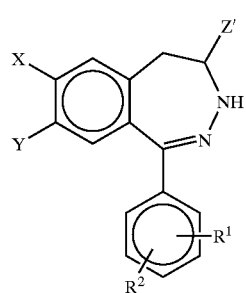

IIa

-continued

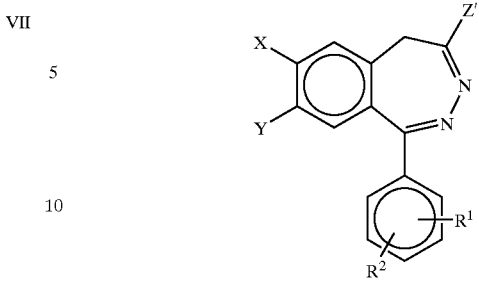

IIIa in which

R$^1$ and R$^2$ are the same or different and mean hydrogen, C$_1$–C$_6$ alkyl, nitro, halogen, cyano, —NR$^8$R$^9$, —O—C$_{1-4}$ alkyl, —CF$_3$, OH or C$_{1-6}$ alkanoyloxy, R$^3$ means hydrogen, halogen, C$_1$–C$_6$ alkoxy, hydroxy, thiocyanato, C$_1$–C$_6$ alkylthio, cyano, COOR$^{12}$, PO$_3$R$^{13}$R$^{14}$, C$_{1-6}$ alkanoyl, C$_{1-6}$ alkanoyloxy, C$_{2-6}$ alkinyl, optionally substituted with C$_{1-4}$ alkoxy or phenyl; C$_{2-6}$ alkenyl, optionally substituted with C$_{1-4}$ alkoxy or phenyl; C$_1$–C$_6$ alkyl, optionally substituted by halogen, hydroxy, C$_1$–C$_6$ alkoxy, C$_1$–C$_6$ thioalkyl, or NR$^{10}$R$^{11}$; C$_{3-7}$ cycloalkyl; monocyclic or bicyclic aryl with 5–12 ring atoms, or monocyclic or bicyclic heteroaryl with 5–12 ring atoms, of which one to three are S,O and/or N, wherein said aryl or heteroaryl is optionally substituted in one to three places in the same way or differently with halogen, C$_{1-4}$ alkoxy or C$_{1-4}$ alkyl, R$^8$ and R$^9$ are the same or different and mean hydrogen, C$_1$–C$_6$ alkyl or —CO—C$_{1-6}$ alkyl, R$^{10}$ and R$^{11}$ are the same or different and mean hydrogen, C$_1$–C$_6$ alkyl or C$_{1-6}$ alkanoyl or together with the nitrogen atom form a 5- to 7-membered saturated heterocycle, which can contain another oxygen, sulfur or nitrogen atom and can be substituted in one to two places with C$_{1-4}$ alkyl or phenyl, R$^{12}$, R$^{13}$, R$^{14}$ are the same or different and mean H or C$_1$–C$_6$ alkyl, X means hydrogen or halogen, Y means C$_{1-6}$ alkoxy or X and Y together mean —O—(CH$_2$)$_n$—O—, n means 1, 2 or 3, and Z″ means —CH$_2$OH, —CHO, —COO—C$_{1-6}$ alkyl, CH$_2$NHR$^3$, or

8. A compound of claim 7, wherein X and Y together mean —O—(CH$_2$)—O—, R$^1$ means hydrogen, and R$^2$ means nitro, at the 4-position of the phenol ring.

9. A compound of claim 7, wherein X and Y together mean —O—(CH$_2$)—O—, and R$^1$ and R$^2$ are hydrogen.

10. A method of making a compound of formula V of claim 1 comprising converting a compound which corresponds to formula V, but has an =O group in place of the =S group, to a compound of formula V by reacting the compound with =O group with diphosphorous pentasulfide.

* * * * *

UNITED STATES PATENT AND TRADEMARK OFFICE
CERTIFICATE OF CORRECTION

PATENT NO. : 6,600,036 B2  Page 1 of 1
DATED : July 29, 2003
INVENTOR(S) : Ernese Csuzdi et al.

It is certified that error appears in the above-identified patent and that said Letters Patent is hereby corrected as shown below:

Column 49,
Line 18, reads "$R^1$ hydrogen" should read -- $R^1$ is hydrogen --

Signed and Sealed this

Fifteenth Day of March, 2005

JON W. DUDAS
*Director of the United States Patent and Trademark Office*